(12) United States Patent
Bruce et al.

(10) Patent No.: US 10,444,950 B2
(45) Date of Patent: Oct. 15, 2019

(54) DUAL SCREEN INTERFACE

(71) Applicant: Gemini Interface Solutions LLC, Fort Collins, CO (US)

(72) Inventors: Robert C. Bruce, Fort Collins, CO (US); Lisa R. Bruce, Fort Collins, CO (US)

(73) Assignee: Gemini Interface Solutions LLC, Fort Collins, CO (US)

( * ) Notice: Subject to any disclaimer, the term of this patent is extended or adjusted under 35 U.S.C. 154(b) by 0 days.

(21) Appl. No.: 14/694,988

(22) Filed: Apr. 23, 2015

(65) Prior Publication Data

US 2015/0227278 A1 Aug. 13, 2015

Related U.S. Application Data

(63) Continuation of application No. PCT/US2014/046156, filed on Jul. 10, 2014.
(Continued)

(51) Int. Cl.
*G06F 3/0484* (2013.01)
*G16H 10/60* (2018.01)
(Continued)

(52) U.S. Cl.
CPC .......... *G06F 3/0484* (2013.01); *G06F 3/0482* (2013.01); *G06F 3/0486* (2013.01);
(Continued)

(58) Field of Classification Search
CPC .... G06F 3/0484; G06F 3/0482; G06F 3/0481; G06F 3/0486; G06F 17/24; G06F 19/00;
(Continued)

(56) References Cited

U.S. PATENT DOCUMENTS 5,568,602 A 10/1996 Callahan et al.
5,920,317 A 7/1999 McDonald
(Continued)

FOREIGN PATENT DOCUMENTS

WO 2012/057835 5/2012
WO WO 2015/006565 1/2015

OTHER PUBLICATIONS

U.S. Appl. No. 61/844,761, filed Jul. 10, 2013.
(Continued)

*Primary Examiner* — Amy Ng
*Assistant Examiner* — William Wong
(74) *Attorney, Agent, or Firm* — Craig R. Miles; CR Miles P.C.

(57) ABSTRACT

A computer implemented dual graphical user interface system having a dual graphical user interface program executable to segregate a patient's medical record into two distinct interacting parts which correspond with the use of a first graphical user interface and a second graphical user interface and correspondingly segregated in a first image display area and a second image display area. The first graphical user interface interactive with the user allows viewing of the cumulative electronic medical records of one or more patients and a second graphical user interface interactive with the user allows entry of information into the electronic medical record of one or more patients. The first and second graphical user interface allowing independent user interaction while interoperably connected to update the first graphical user interface with patient data entered into the second graphical user interface.

20 Claims, 21 Drawing Sheets

Related U.S. Application Data

(60) Provisional application No. 61/844,761, filed on Jul. 10, 2013.

(51) Int. Cl.
*G06Q 50/24* (2012.01)
*G06F 3/0481* (2013.01)
*G06F 3/0482* (2013.01)
*G06F 3/0486* (2013.01)
*G06F 17/24* (2006.01)

(52) U.S. Cl.
CPC ........ *G06F 3/04817* (2013.01); *G06F 17/243* (2013.01); *G06Q 50/24* (2013.01); *G16H 10/60* (2018.01)

(58) Field of Classification Search
CPC ... G06F 3/04817; G06F 17/243; G16H 10/00; G16H 10/60; G06Q 50/24
See application file for complete search history.

(56) References Cited

U.S. PATENT DOCUMENTS

| | | |
|---|---|---|
| 7,424,679 B1 | 9/2008 | Lamer et al. |
| 7,545,627 B1 | 6/2009 | Lantigua |
| 7,996,754 B2 | 8/2011 | Bodin et al. |
| 8,185,494 B2 | 5/2012 | Davis et al. |
| 8,271,574 B1 | 9/2012 | Srinivasan et al. |
| 8,305,293 B2 | 11/2012 | Chu |
| 8,326,651 B2* | 12/2012 | McLaren ............... G06Q 10/06 705/3 |
| 9,544,993 B2 | 1/2017 | Lee et al. |
| 2001/0041991 A1* | 11/2001 | Segal .................... G06F 19/321 705/3 |
| 2002/0095424 A1* | 7/2002 | Chung .................. G06F 19/322 |
| 2002/0161795 A1* | 10/2002 | O'Rourke ............. G06F 19/322 715/205 |
| 2003/0140044 A1* | 7/2003 | Mok ....................... G06Q 50/22 |
| 2003/0187615 A1* | 10/2003 | Epler .................... G06F 19/3443 702/181 |
| 2004/0083217 A1* | 4/2004 | Brackett ............. G06F 19/3443 |
| 2004/0111296 A1* | 6/2004 | Rosenfeld ............ G06F 19/322 705/2 |
| 2004/0172300 A1* | 9/2004 | Mihai .................. A61B 5/0002 705/2 |
| 2005/0052835 A1 | 3/2005 | Wu et al. |
| 2005/0091082 A1* | 4/2005 | Garber .................. G06Q 50/22 705/2 |
| 2005/0149364 A1* | 7/2005 | Ombrellaro ........... A61B 5/103 705/3 |
| 2005/0183023 A1* | 8/2005 | Maruyama ............. A47B 21/00 715/759 |
| 2005/0257145 A1* | 11/2005 | Gage ..................... G06F 1/1601 715/273 |
| 2005/0267351 A1* | 12/2005 | Humphrey ............ G06F 19/321 600/408 |
| 2006/0034427 A1* | 2/2006 | Brooks .................. A61B 6/563 378/198 |
| 2006/0206825 A1* | 9/2006 | Dorn ..................... G06F 3/0481 715/761 |
| 2007/0041151 A1 | 2/2007 | Park |
| 2007/0067186 A1* | 3/2007 | Brenner ................. G06Q 50/22 705/2 |
| 2007/0188450 A1* | 8/2007 | Hernandez ............ G06F 1/1626 345/158 |
| 2008/0021736 A1* | 1/2008 | Elizabeth ............... G06Q 50/24 705/2 |
| 2008/0065420 A1 | 3/2008 | Tirinato et al. |
| 2008/0065422 A1 | 3/2008 | Weber |
| 2008/0077431 A1* | 3/2008 | Calder .................. G06Q 10/06 705/2 |
| 2008/0119731 A1* | 5/2008 | Becerra ................... A61B 8/00 600/437 |
| 2008/0154646 A1 | 6/2008 | Barrett et al. |
| 2008/0294454 A1* | 11/2008 | Taha ..................... G06F 1/1616 705/2 |
| 2009/0076856 A1 | 3/2009 | Darby et al. |
| 2009/0178008 A1 | 7/2009 | Herz et al. |
| 2010/0156913 A1* | 6/2010 | Ortega .................. G06F 3/1438 345/520 |
| 2010/0182265 A1* | 7/2010 | Kim ..................... G06F 1/1616 345/173 |
| 2011/0187662 A1* | 8/2011 | Lee ........................ G06F 1/1641 345/173 |
| 2012/0188147 A1 | 7/2012 | Hosein et al. |
| 2012/0200489 A1* | 8/2012 | Miyashita ............. G06F 3/0233 345/156 |
| 2012/0232929 A1* | 9/2012 | Experton ............... G06Q 10/06 705/3 |
| 2012/0253851 A1* | 10/2012 | Phillips .................. G06Q 50/24 705/3 |
| 2012/0278734 A1* | 11/2012 | Ishizuka ............... G06F 1/1624 715/752 |
| 2013/0085498 A1 | 4/2013 | Spatola et al. |
| 2013/0085798 A1* | 4/2013 | Spatola .................. G06Q 10/06 705/7.24 |
| 2014/0067012 A1* | 3/2014 | Drees ................. A61N 1/37247 607/59 |
| 2014/0101577 A1* | 4/2014 | Kwak ................... G06F 1/1618 715/761 |
| 2014/0194760 A1* | 7/2014 | Albert .................. A61B 5/0402 600/509 |
| 2014/0207686 A1* | 7/2014 | Experton ............ G06F 19/3418 705/51 |
| 2015/0228217 A1 | 8/2015 | Perdices-Gonzalez et al. |

OTHER PUBLICATIONS

International Patent Cooperation Treaty Patent Application No. PCT/US14/46156, filed Jul. 10, 2014.
Int'l PCT Patent Application No. PCT/US14/46156; International Search Report and Written Opinion of the International Searching Authority, dated Jan. 28, 2015, 11 total pgs.
AMA. Quality of Patient Care Drives Physician Satisfaction; Doctors Have Concerns about Electronic Health Records, Study Finds. Website, http://ama-assn.org, originally downloaded Apr. 4, 2014, 2 pages total.
EHR Intelligence. Certified EHR Technology. Website, http://ehrintelligence.com, originally downloaded Aug. 14, 2013, 2 pages total.
EHR Intelligence. EHR Incentive Programs. Website, http://ehrintelligence.com, originally downloaded Aug. 14, 2013, 2 pages total.
EHR Intelligence. Independent docs not optimistic about accountable care, EHRs. Website, http://ehrintelligence.com, originally downloaded Aug. 14, 2013, 2 pages total.
EHR Intelligence. Meaningful Use. Website, http://ehrintelligence.com, originally downloaded Aug. 14, 2013, 2 pages total.
EHR Intelligence. Office of the National Coordinator for Health Information Technology. Website, http://ehrintelligence.com, originally downloaded Aug. 14, 2013, 2 pages total.
Gabl. Meaningful Use and Medical Assistants: What Does this Mean for their Career? AMT Events, Jun. 2014, pp. 86-89.
Garets et al. Electronic Medical Records vs. Electronic Health Records: Yes, There Is a Difference. A HIMSS Analytics™ White Paper. Jan. 2006, 14 pages total.
Garets et al. Electronic Patient Records. EMRs and EHRs. Concepts as different as apples and oranges at least deserve separate names. Healthcare Informatics, Oct. 2005, 22(10), pp. 1-4.
Medical Economics. 4 ways EHR vendors are building better systems. Website, http://medicaleconomics.modernmedicine.com, originally downloaded Oct. 9, 2014, 10 pages.
Medical Economics. Top 50 EHR software companies of 2015. Website, http://medicaleconomics.modernmedicine.com, originally downloaded Oct. 9, 2014, 11 pages total.

(56) References Cited

OTHER PUBLICATIONS

U.S. Department of Health and Human Services. Summary of the NHIN Prototype Architecture Contracts. A Report for the Office of the National Coordinator for Health IT. May 2007, 113 pages, Gartner, Inc.

Wikipedia. American Recovery and Reinvestment Act of 2009. Website, http://en.wikipedia.org, originally downloaded Aug. 14, 2013, 26 pages total.

Wikipedia. Multitier architecture. Website, http://en.wikipedia.org, originally downloaded Apr. 14, 2015, 6 pages total.

* cited by examiner

FIG. 3

PATIENT: SMITH, DAVID    DOB: 07/16/1998 (MALE) - 05/11/2014  11:40 MDT

LAKE COUNTY CLINIC ▶  FRANK JONES, MD ▶

04/18/2014 10:42 AM X  Patient Demographics X

Patient Information

- Last name: Smith
- First name: Brad
- MI:
- Previous last name:
- Nickname:
- ★ Social Security Number
- Other ID:
- Account #: 55124010
- MRN: 00080011782

- Birth date: 07/15/1998
- Sex: M
- For cardiology only:
  - Fact Sheet
  - App
  - Report
- Marital Status: Single
- Spouse name:
- PCP/Insurance/Pharmacies
- PCP:
- ★ Consent
- ▲ Providers

- Address: 1234 Any Street
- 1st visit:
- Last visit:
- Next visit:
- Race:
- Referred by:
- City: Anytown
- State: CO  Zip: 12345
- Language:
- Insurance:
- ★ Secondary Address
- Ethnicity:
- Pharmacy #1:
- County: AnyCounty
- Religion:
- Address:
- Phone:
- Blood Type:
- City:
- State: Zip:
- Home: XXX-XXX-XXXX
- Employment Cancel
- Phone: XXX-XXX-XXXX
- Fax:
- Work: XXX-XXX-XXXX  Extension:
- Cell: XXX-XXX-XXXX
- Pharmacy #2:
- Alternate:
- Type:
- Address:
- Email:
- Preferred contact method:
- Electronic Communication ID:
- ▲ Patient Relationships
- Emergency Contact:
- Relationship:
- Last name:
- First name:

History | Demographics | Maintenance

☐ Adult Chart Sum.
☐ Adult Chart Sum. LCC
☐ CARD Doctor Dsts
☐ CARD HIPPA
☐ Card Last PE LCC 792
☐ Chart Notes
☐ Chart Tracing
☐ CHSCommunityPortal
☐ CHSParticipSettings
☐ CQQ II Particip
☐ Last Physical Exam
☐ Lipid Clinic Date
☐ Master Demo. Temp
☐ Medication History
☐ OS Demographics
☐ Order Administration
☐ Ort Chart Summary
☐ Patient Demographics
☐ Patient Demo. LCC
☐ PHI Log LCC 792
☐ HHE Drug Study
☐ Uro Cancer Summary

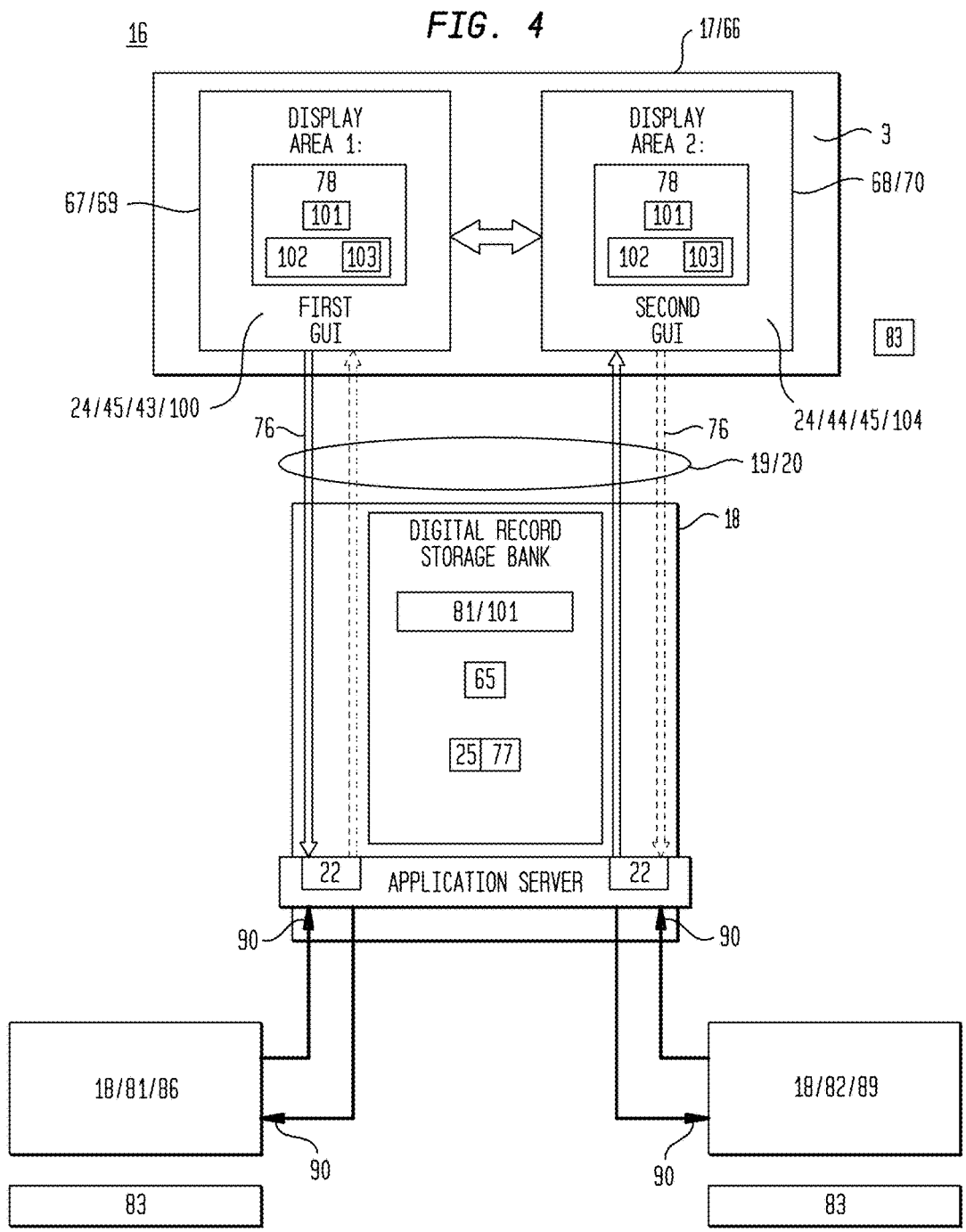

FIG. 5

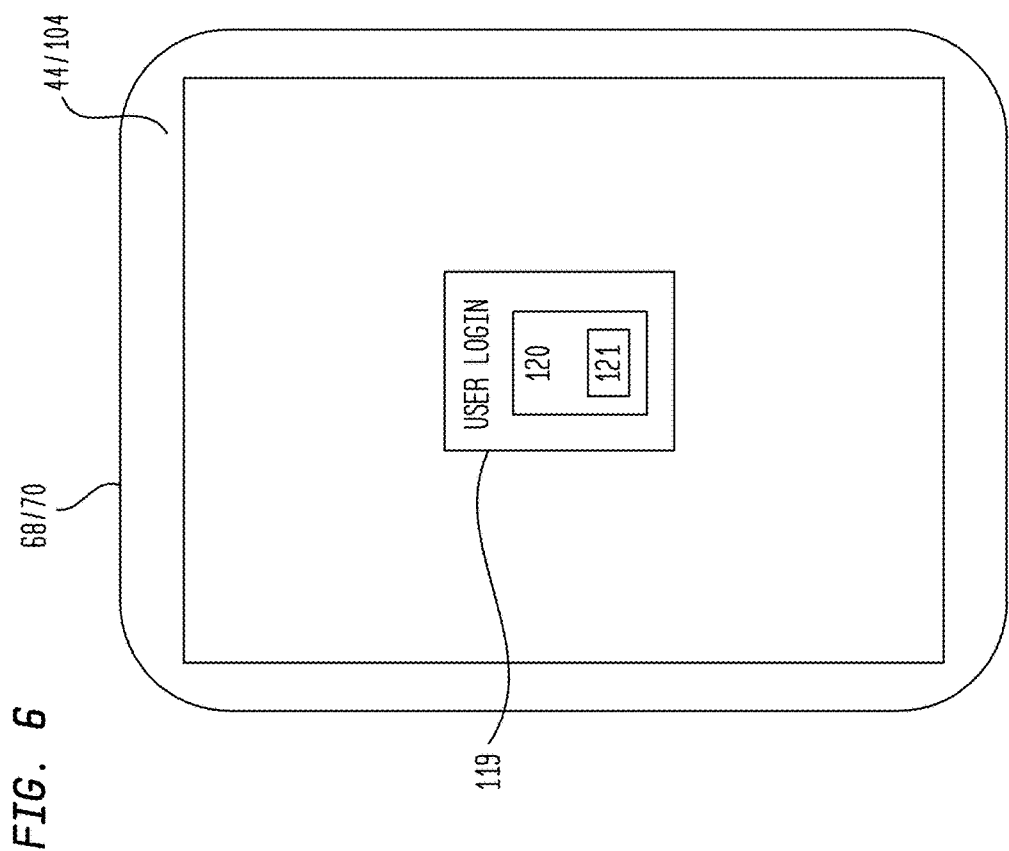
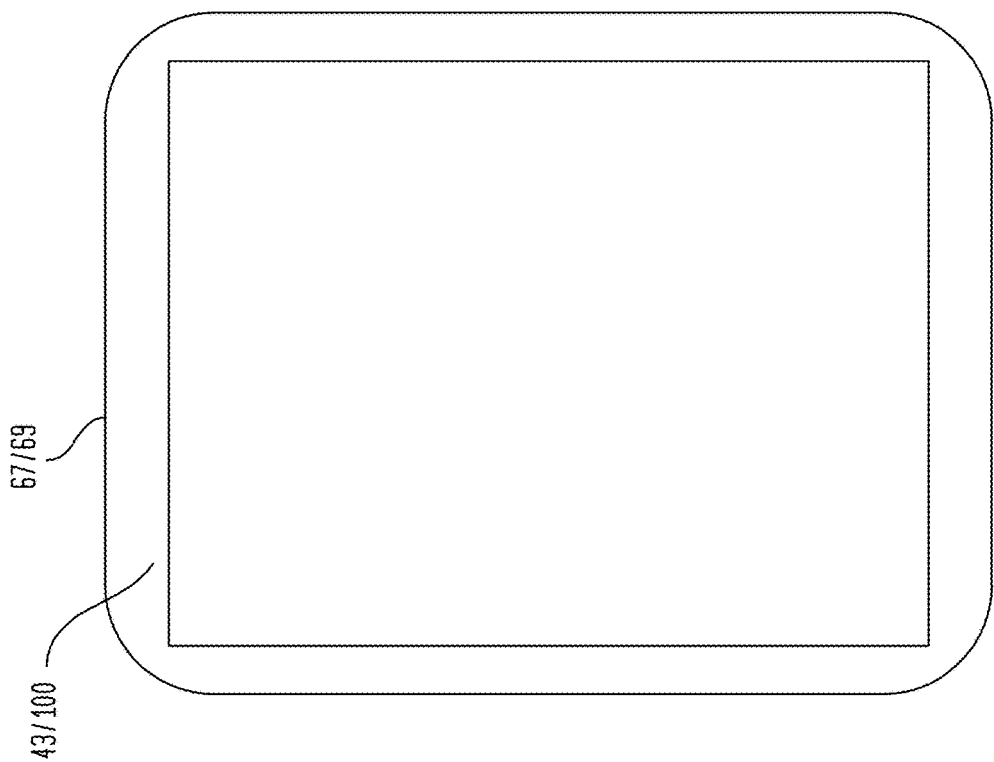
FIG. 6

FIG. 7

Inbox    TO DO LIST
Medical Question    Billy Jack (5-30-02)
Document Review     Mary Smith (3-10-99)
Rx Refill           Daniel Elder (2-225-03)
Rx Refill           Charlie Hanes (1-11-18)
Medical Question    Laura Baker (8-22-13)

Meaningful Use Report Card
For
Dr. Frank Jones, M.D.
(Auto Updated 02-17-2014)
[View Report]

PC MODE

Inbox    CLINIC SCHEDULE    2-23-2014
0800  David Smith       9 yo     Cough/Wheeze
0820  William Fold      3 yo     Well Check
0840  Jose Martinez     18 mo    Well Check
0910  Hannah Davis      15 yo    Fever/ST
0920  Robert Frappels   8 yo     ADHD F/U
0940  Phillip DeGlass   6 yo     ADHD (new)
1040  Sam Jones         4 mo     Cough
1100  Lilly White       2 wk     Well Baby
1120  Ron deVu          17 yr    Headaches
                    Lunch Break
1330  Joe Kuhl          3 yr     Well Check
1345  Suzie Chu         8 yr     Rash
1400  Jack Hammer       4 yr     Contusion
1420
1440  Daniel Druff      10 yr    Itchy scalp
1500
1520  Arnold Chiari     7 yr     Headache
1540  Liz Franke        15 yr    Foot injury
1600
1620  Mary Lamb         12 yr    Well Check
1640  Tommy John                 Elbow pain

[SELECT PATIENT]

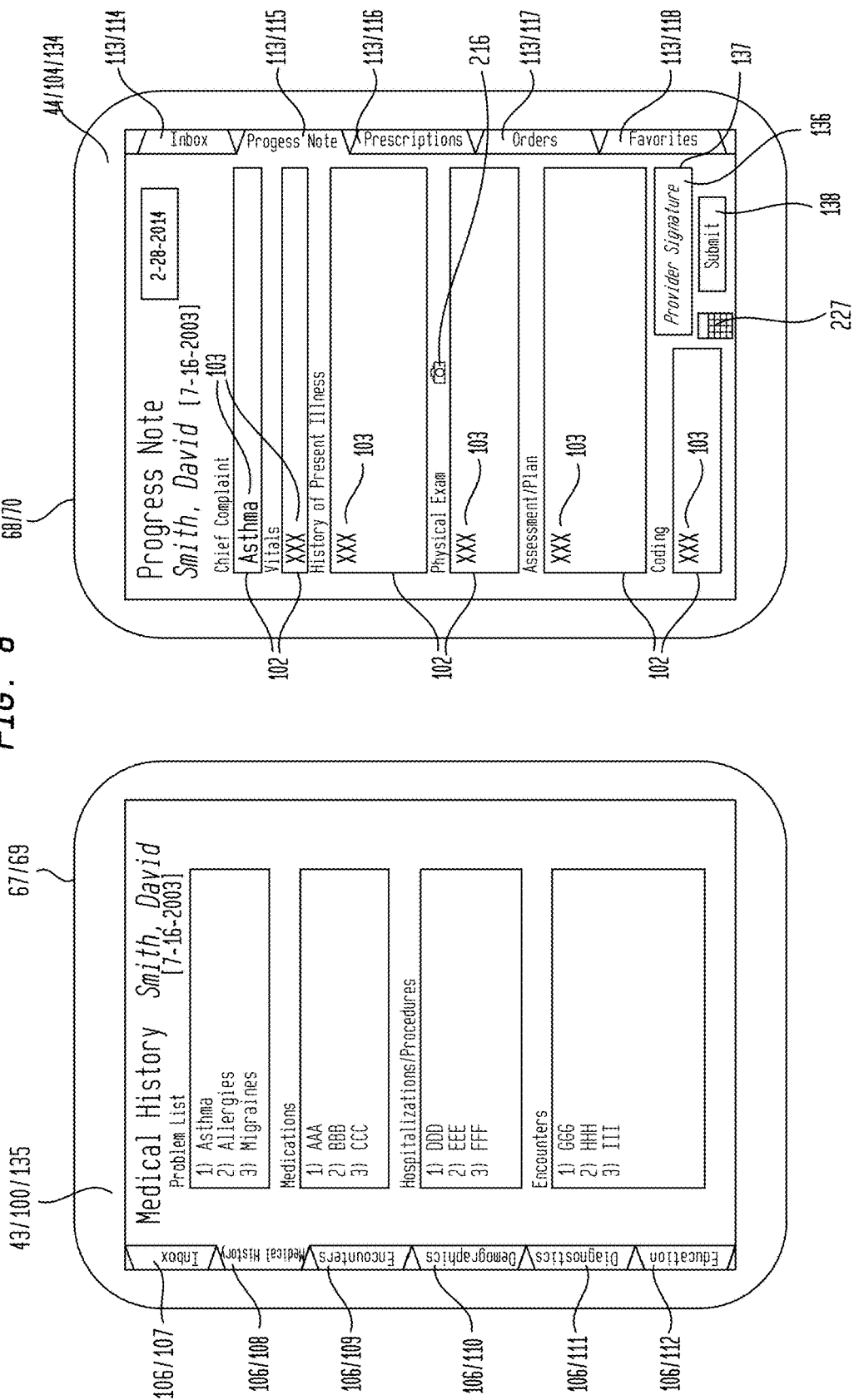

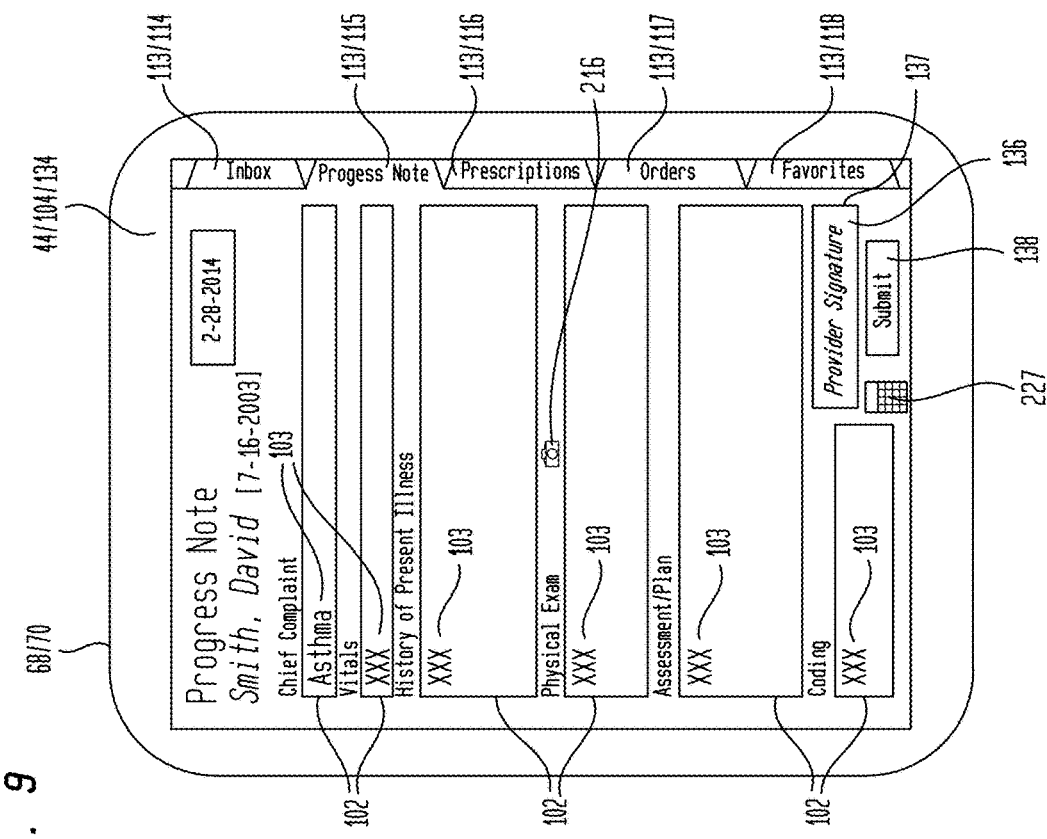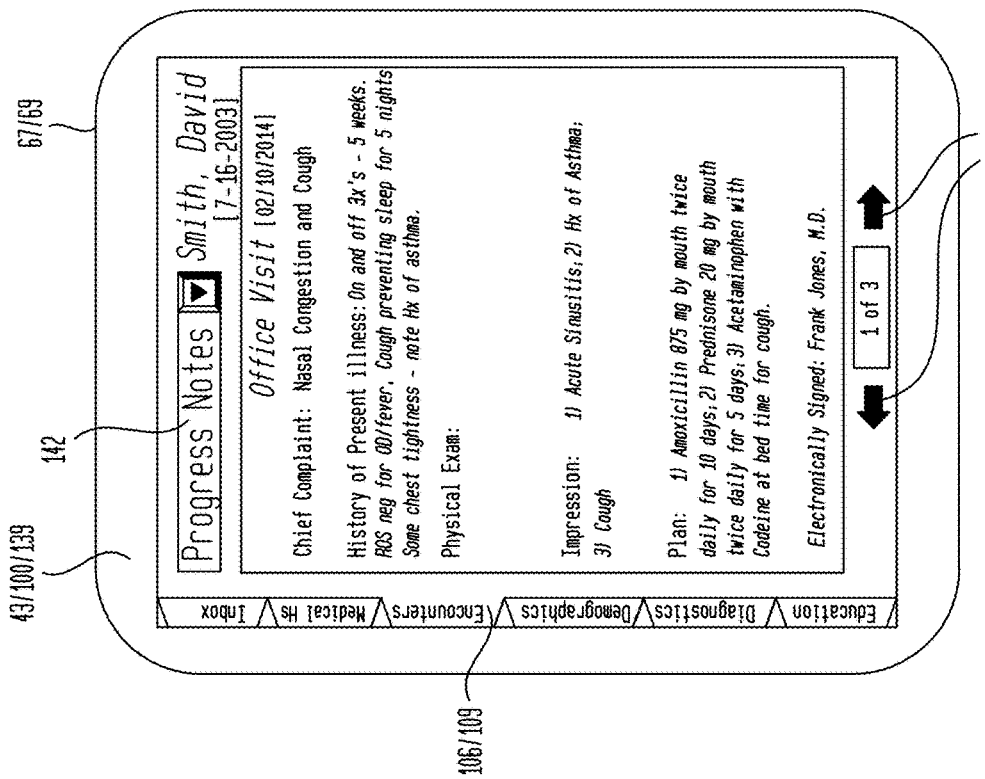
FIG. 9

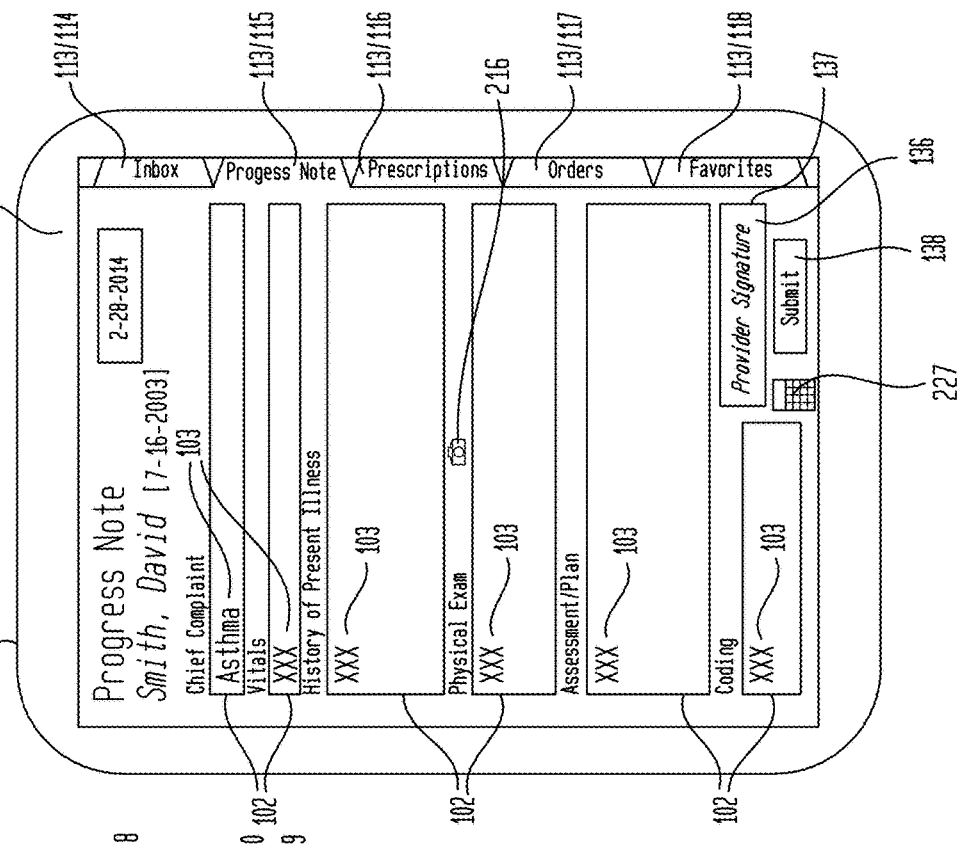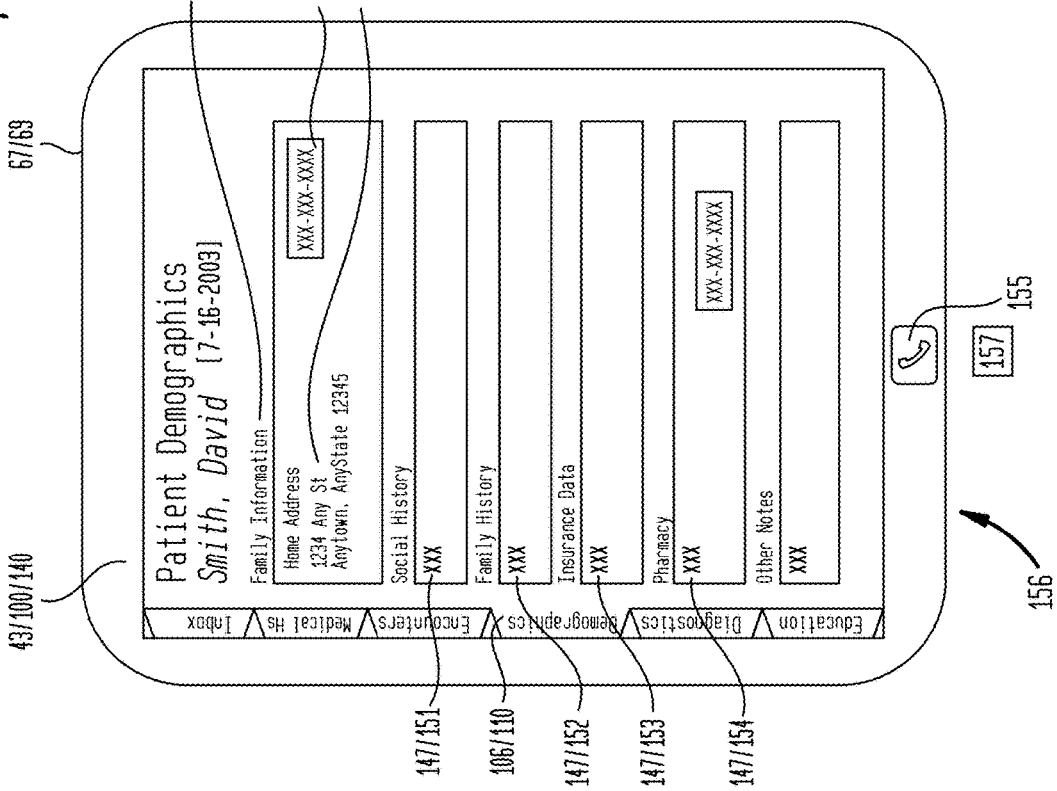
FIG. 10

FIG. 14

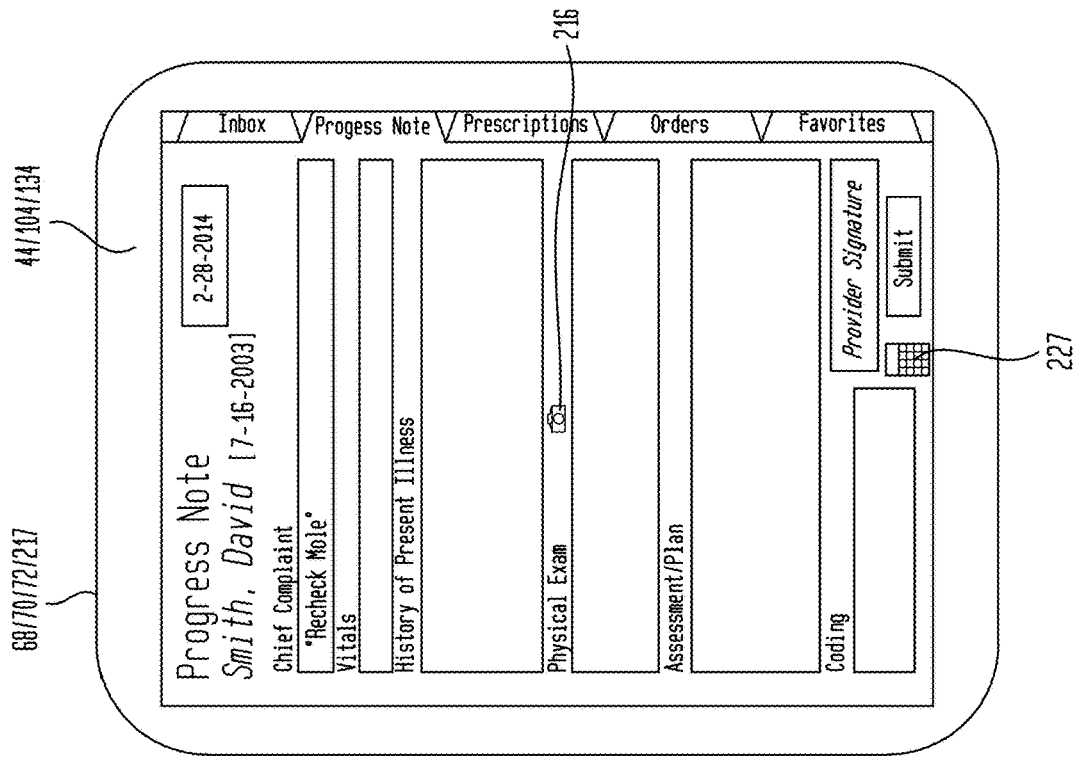
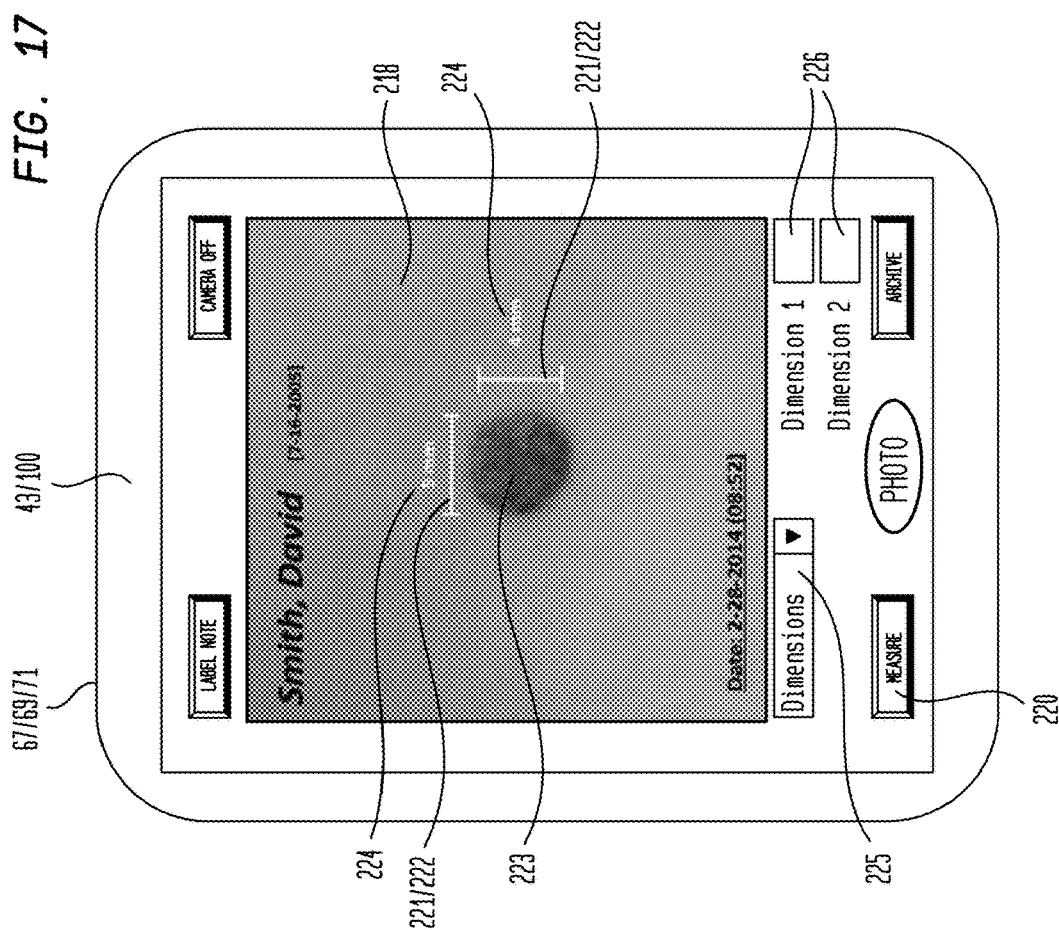
FIG. 17

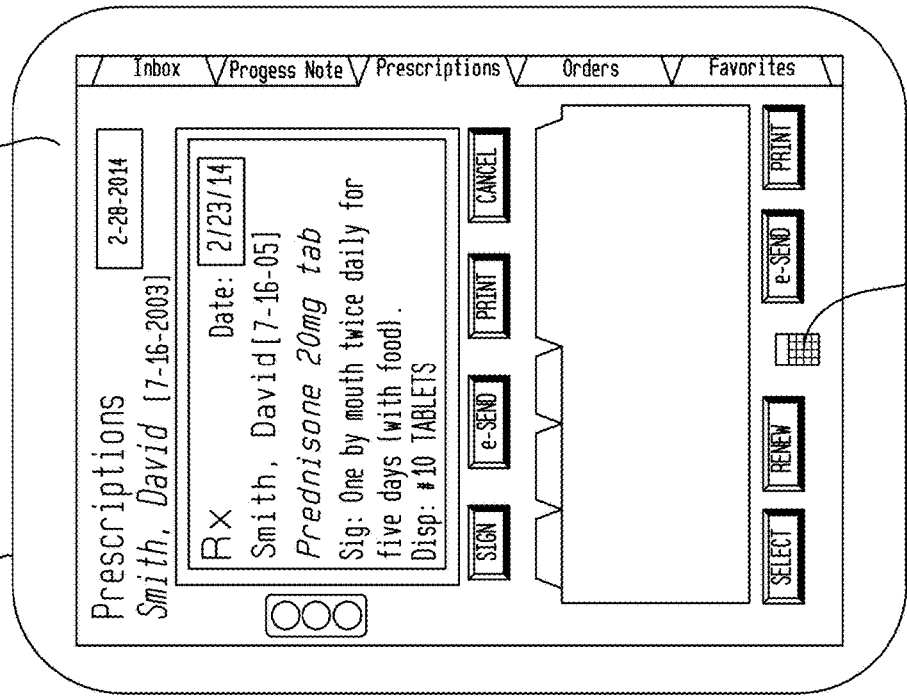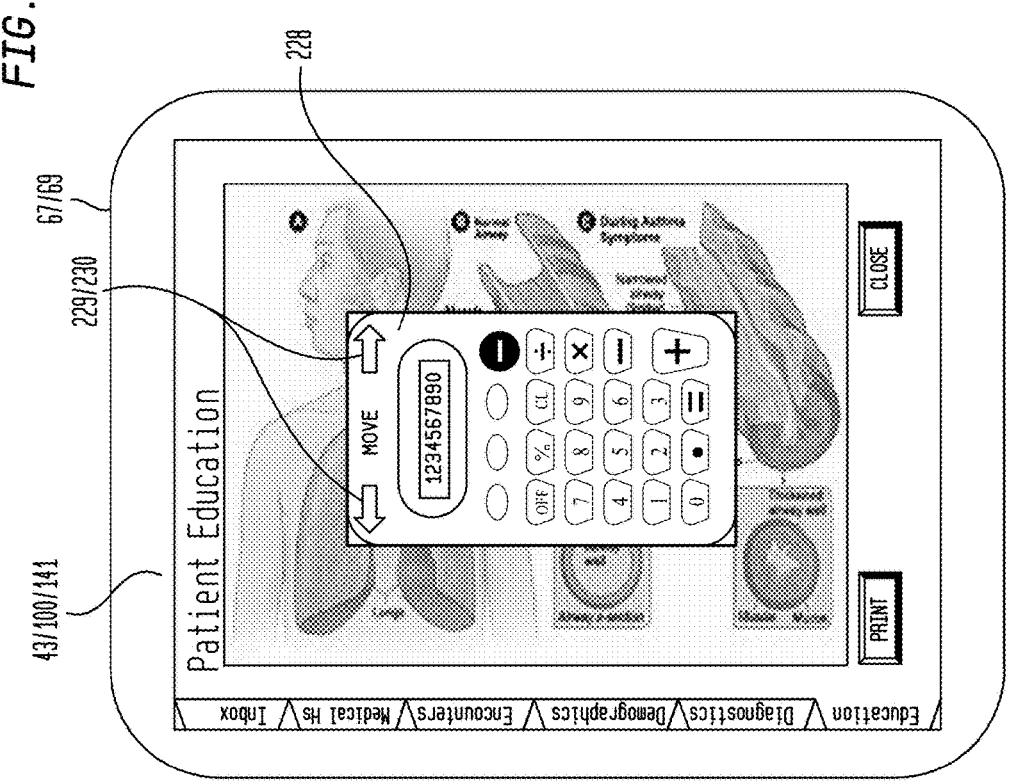
FIG. 18

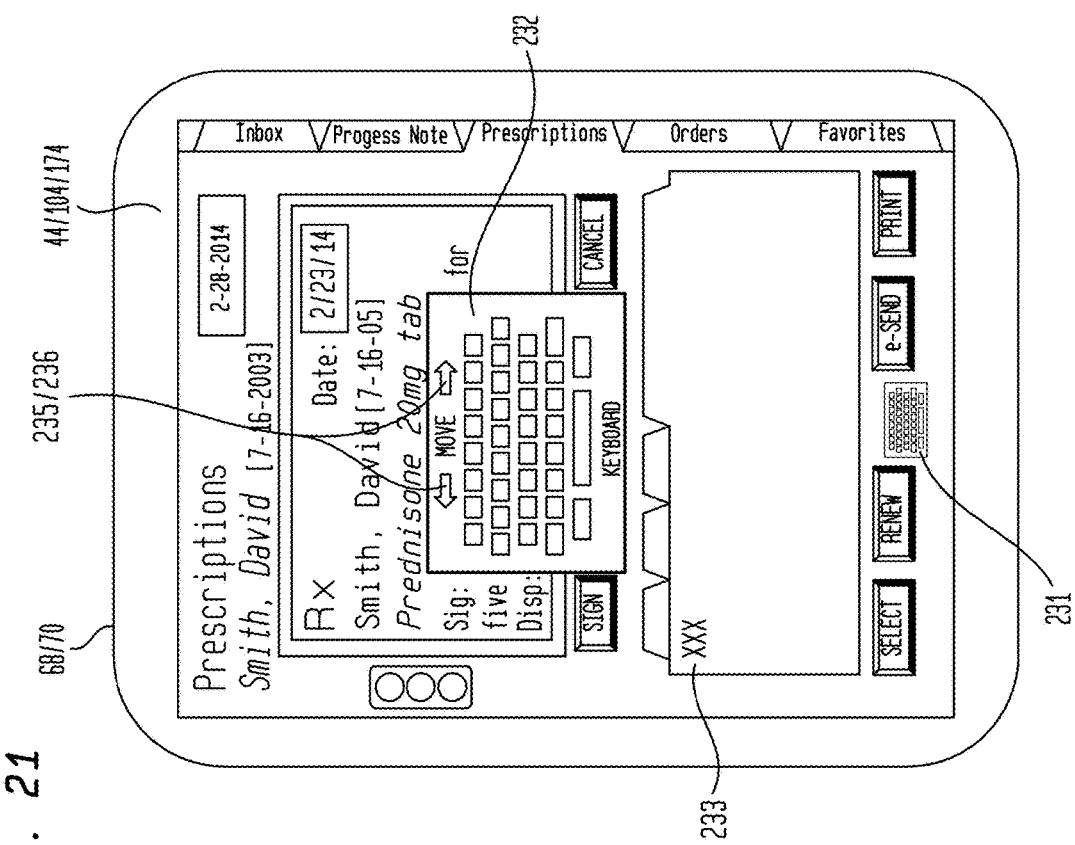
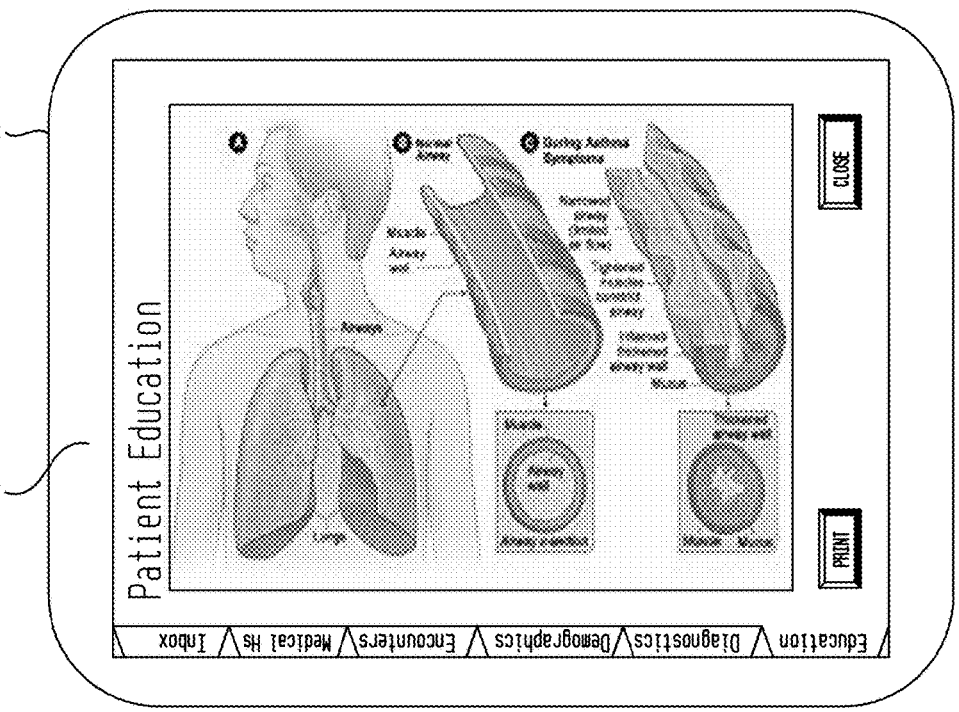
FIG. 21

DUAL SCREEN INTERFACE

This United States Patent Application is a continuation of International Patent Cooperation Treaty Patent Application No. PCT/US14/46156, filed Jul. 10, 2014, which claims the benefit of U.S Provisional Patent Application No. 61/844,761, filed Jul. 10, 2013, each hereby incorporated by reference herein.

I. BACKGROUND OF THE INVENTION

A inventive computer-implemented dual graphical user interface system having a dual graphical user interface program executable to segregate a patient's medical record into two distinct interacting parts which correspond with the use of a first graphical user interface and a second graphical user interface correspondingly segregated in a first image display area and a second image display area. The first graphical user interface interactive with a user allows viewing of the cumulative electronic medical record of one or more patients and the second graphical user interface interactive with the user allows entry of information into the electronic medical record of one or more patients. The first and second graphical user interfaces allow independent user interaction while interoperably connected to update the first graphical user interface with patient data entered into the second graphical user interface.

Currently available electronic medical record systems have significant shortcomings as it pertains to providing an efficient, intuitive electronic substitution for paper records of patient information. Numerous accounts, from popular media to medical publications, describe the myriad of ways in which electronic medical record implementation has been credited with losses in revenue for medical practices and healthcare professionals not only due to costly implementation, but also due to substantially decreased numbers of patient visits caused by inefficient and cumbersome electronic medical record keeping. Government mandates designed to create universal adoption of electronic medical records throughout the United States have imposed unrealistic deadlines on medical practices, with financial penalties for failing to comply. Medical healthcare professionals may be experiencing increased symptoms of burnout, career dissatisfaction, and even early retirement, secondary to the added demands of electronic medical record implementation.

Now referring primarily to FIG. 1, an illustrative example of a conventional electronic medical records graphical user interface (1) is shown in which a patient encounter template (2) opened by user interaction may fill substantially the entire display surface (3), and a patient history window (4) opened by user interaction may fill the remaining portion of the display surface (3). The patient history window (4) may display past patient encounters (5) in the form of a patient history list (6) in which each past patient encounter (5) has only a date identifier (7) and a time identifier (8). This conventional form of a patient history window (4) may be without an identifier or description as to what the past patient encounter (5) related to, such as a telephone call identifier or an office visit identifier. Furthermore, the conventional patient history window (4) does not include any information relating to medical history, medical diagnoses, medications, or otherwise.

Now referring primarily to FIG. 2, in the same illustrative example of a conventional electronic medical records graphical user interface (1), a first patient history template Sep. 28, 2012 10:42 AM (9) and a second patient history template Dec. 15, 2012 11:02 AM (10) have by user interaction been opened. Both the first patient history template Sep. 28, 2012 10:42 AM (9) and the second patient history template Dec. 15, 2012 11:02 AM (10) overlay the present encounter template (11) each filling substantially the entire display surface (3) with the patient history window (4) filling the remaining portion of the display surface (3). This illustrates a disadvantage of conventional electronic medical records graphical user interfaces (1), in that the user cannot view and make entries to the patient encounter template (2) without first performing various interactions in the conventional electronic medical records graphical user interface (1) in order to close or otherwise remove the overlying first and second patient history templates (9)(10).

Now referring primarily to FIG. 3, which shows an illustrative example of a conventional electronic medical records graphical use interface (1) which by user interaction a patient demographics window (12) has been opened to fill a right side portion of the display surface (3). By user interaction in the patient demographics window (12), a patient demographics template (13) can be opened to overlay the patient encounter window (5), and in the first instance, resulting in the same disadvantage above described in which the user cannot view and make entries to the patient encounter template (2) without first closing the overlaying patient demographics template (13). Additionally, in the instant example, the patient demographics template (13) cannot be viewed by the user in the entirety because the display area of the patient demographics template (13) exceeds the display area of the display surface (3). The user must further interact with the conventional electronic medical records graphical user interface (1), in this example a scroll bar (14), to view other portions of the patient demographics template (13). Additionally, in this example, the user may have opened the patient demographics template (13) for the purpose of obtaining a telephone number (15) to communicate with the patient; however, there is no provision in the patient demographics template (13) to document information relevant to telephone communication with the patient. In order to document the telephone communication, the patient demographics template (13) must be closed and another template in the patient record must be opened.

II. DISCLOSURE OF INVENTION

Accordingly, a broad object of the invention can be to provide a computer-implemented dual graphical user interface program executable to segregate the electronic medical record of a patient into two distinct interacting parts which correspond with the use of a first graphical user interface and a second graphical user interface correspondingly segregated in a first image display area and a second image display area. The first graphical user interface interactive with a user allows viewing of the cumulative electronic medical records of one or more patients while the second graphical user interface interactive with a user allows entry of information into the electronic medical record of one or more patients. This provides an advantage in that the user can view past medical records of the patient in the first graphical user interface while entering information into the medical record of the patient in the second graphical user interface. Entry of information in the second graphical user interface can be contemporaneously viewed as part of the past medical record in the first graphical user interface.

Another broad object of the invention can be to provide computer elements including one or more server computers each having a server memory which contains electronic medical records of a plurality of patients and at least one of the plurality of server computers contains the dual graphical user interface program executable to segregate electronic medical records of a plurality patients into two distinct interacting parts used in association with the first graphical user interface displayed in a first image display area and the second graphical user interface displayed in a second image display area and as to particular embodiments the first image display area and the second image display area can be correspondingly located on discrete first and second display surfaces for concurrent mutual or discrete viewing by one or more users.

Another broad object of the invention can be to provide a method of managing electronic medical records in which a dual graphical user interface program segregates a patient's medical record into two distinct interacting parts for corresponding use in association with a first graphical user interface which by user interaction allows viewing of the electronic medical record of the patient and a second graphical user interface which by user interaction allows entry to the electronic medical record of a patient.

Another broad object of the invention can be to provide a method of using electronic medical records in which the user by interaction in a first graphical user views the electronic medical record of the patient including the entries made into the second graphical user interface and a second graphical user interface in which a user enters patient information into the electronic medical record of the patient.

Naturally, further objects of the invention are disclosed throughout other areas of the specification and drawings.

III. BRIEF DESCRIPTION OF THE DRAWINGS

FIG. 3 is an illustrative example of a conventional electronic medical record graphical use interface depicting a patient demographics template opened overlaying a first patient history template Sep. 28, 2012 10:42 AM.

FIG. 4 is a block diagram of a particular embodiment of the inventive dual interface electronic medical records management system.

FIG. 5 is a block diagram of illustrative computer elements, network elements, and a computer-readable medium containing a computer code which provides computer-executable instructions to provide embodiments of the inventive dual interface electronic medical records management system.

FIG. 6 is an illustration of a particular embodiment of a first graphical user interface image and a second graphical user interface image displayed on corresponding discrete first and second display surfaces by execution of an inventive dual graphical user interface program.

FIG. 7 is an illustration of a particular embodiment of a first graphical user interface image and a second graphical user interface image displayed on corresponding discrete first and second display surfaces by execution of an inventive dual graphical user interface program.

FIG. 8 is an illustration of a particular embodiment of a first graphical user interface image and a second graphical user interface image displayed on corresponding discrete first and second display surfaces by execution of an inventive dual graphical user interface program.

FIG. 9 is an illustration of a particular embodiment of a first graphical user interface image and a second graphical user interface image displayed on corresponding discrete first and second display surfaces by execution of an inventive dual graphical user interface program.

FIG. 10 is an illustration of a particular embodiment of a first graphical user interface image and a second graphical user interface image displayed on corresponding discrete first and second display surfaces by execution of an inventive dual graphical user interface program.

FIG. 14 is an illustration of a particular embodiment of a first graphical user interface image and a second graphical user interface image displayed on corresponding discrete first and second display surfaces by execution of an inventive dual graphical user interface program.

FIG. 17 is an illustration of a particular embodiment of a first graphical user interface image and a second graphical user interface image displayed on corresponding discrete first and second display surfaces by execution of an inventive dual graphical user interface program.

FIG. 18 is an illustration of a particular embodiment of a first graphical user interface image and a second graphical user interface image displayed on corresponding discrete first and second display surfaces by execution of an inventive dual graphical user interface program.

FIG. 21 is an illustration of a particular embodiment of a first graphical user interface image and a second graphical user interface image displayed on corresponding discrete first and second display surfaces by execution of an inventive dual graphical user interface program.

IV. MODE(S) FOR CARRYING OUT THE INVENTION

Figure 5:
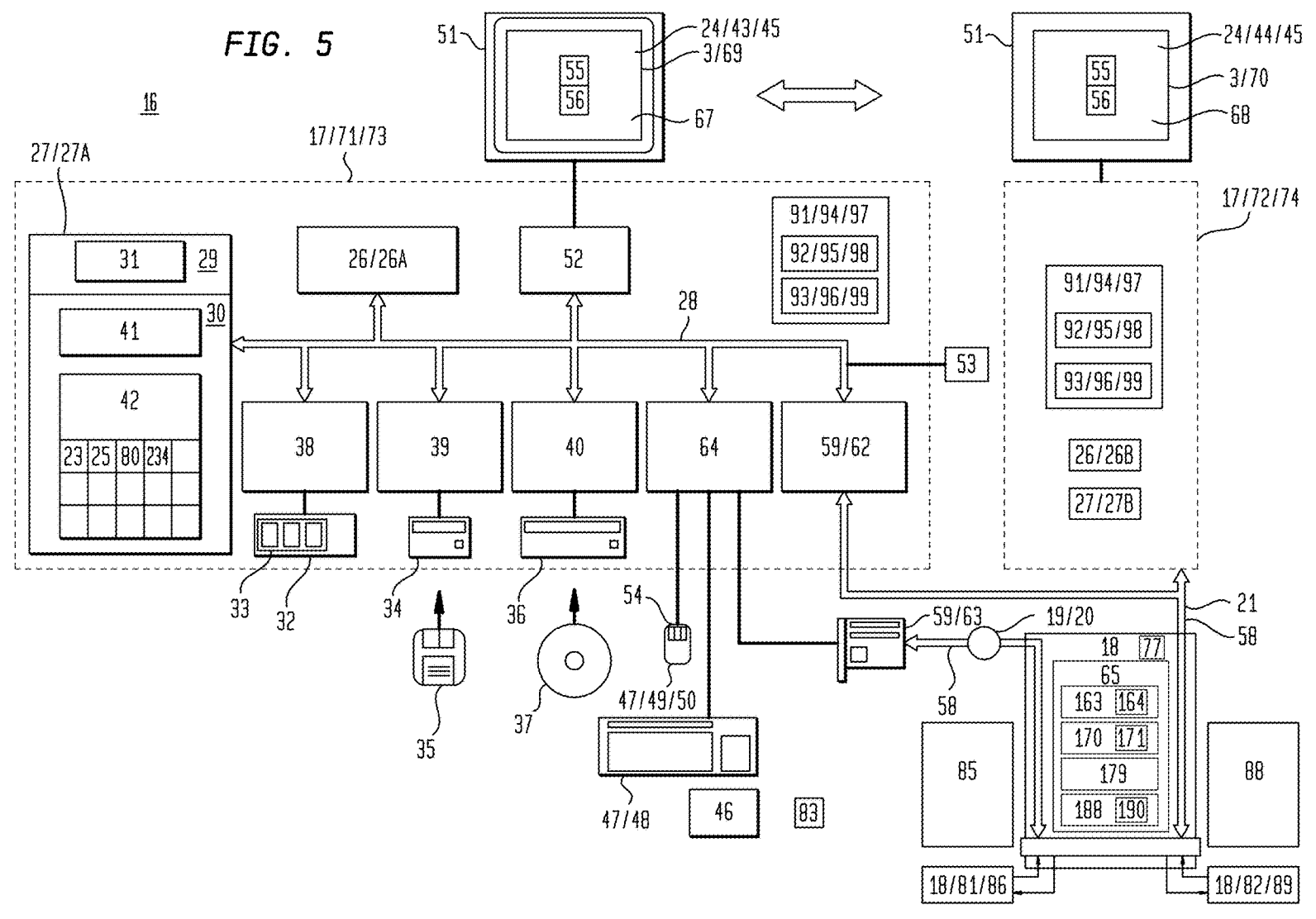
Figure 1:
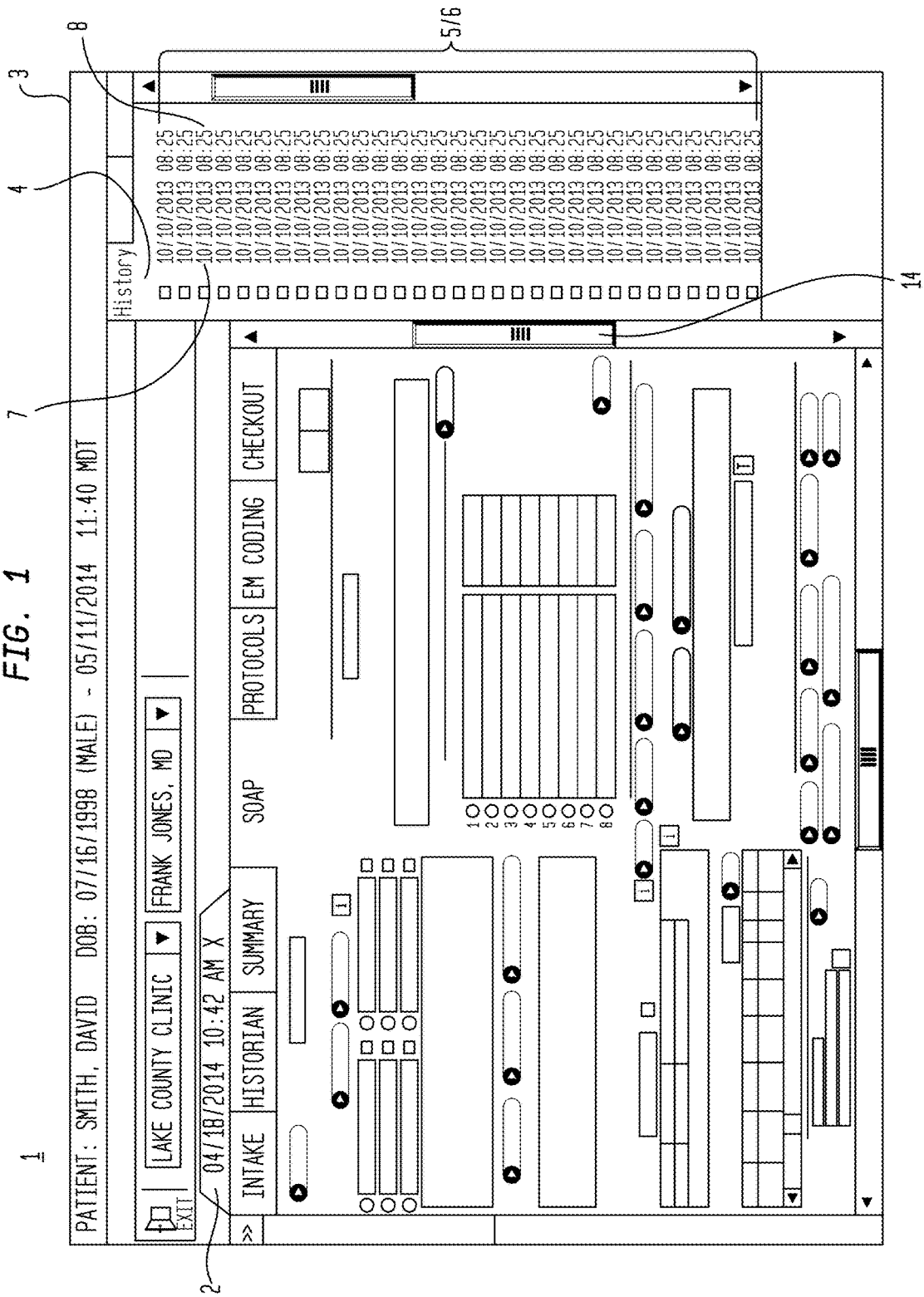
FIG. 1 is an illustrative example of a conventional electronic medical record graphical user interface.

Now referring primarily to FIG. 4 and FIG. 5, which generally illustrate computer elements, certain network elements, computer-readable media, and a computer code which can be utilized to practice embodiments of the inventive dual interface electronic medical records management system (16). It is not intended that embodiments of the invention be practiced in only wide area computing environments or only in local computing environments, but rather the invention can be practiced in local computing environments or in distributed computing environments where functions or tasks can be performed by remote processing devices that are linked through a communications network. In a distributed computing environment, program modules may be located in both local or remote memory storage device(s) or device element(s).

Also while a preferred embodiment of the invention is described in the general context of computer-executable instructions such as a program and program modules which utilize routines, programs, objects, components, data structures, or the like, to perform particular functions or tasks or implement particular abstract data types, or the like, being executed by the computer elements and network elements, it is not intended that any embodiments of the invention be limited to a particular set of computer-executable instructions or protocols.

Now referring to primarily to FIG. 4, one or more client computers (17) can be configured to connect with one or more server computers (18) through a wide area network "WAN" (19) (such as the World Wide Web of the Internet (20)), or through one or more local area networks ("LAN") (21) to transfer corresponding data (22) (quantities, characters, or symbols on which operations are performed by a computer). As to particular embodiments, the client computer (17) can take the form of a limited-capability computer designed specifically for navigation on the Internet (20). Alternatively, the client computer (17) might be a set-top box, an intelligent television connected to receive data (22) through an entertainment medium such as a cable television network or a digital satellite broadcast, a hand-held device such as a smart phone, a slate or pad computer, a personal digital assistant or camera/cell phone, or a multiprocessor system, a microprocessor-based or programmable consumer electronic, a network personal computer, a minicomputer, a mainframe computer, or the like.

Again, referring primarily to FIG. 4 and FIG. 5, the client computer (17) can include an Internet browser (23) such as MICROSOFT's INTERNET EXPLORER, GOOGLE CHROME, MOZILLA, FIREFOX, or the like, which functions to download and render multimedia content that is formatted in "hypertext markup language" (HTML). In this environment, the server computer (18) might be programmed to implement the most significant portions of the inventive dual graphical user interface (24). As to these embodiments, a dual graphical user interface program (25) (also referred to as a "computer code") executed to provide the functions of the dual graphical user interface (24) can be resident in the server computer (18) (as shown in the example of FIG. 4) and the client computer (17) can use the Internet browser (23) to simply display downloaded content and to relay user inputs back to the server computer (18). The server computer (18) would respond by formatting or populating one or more dual graphical user interfaces (24) (see for example FIG. 6 through FIG. 19) and downloading them for display on the client computer (17).

In other embodiments, the server computer (18) can be used primarily as a source of data (22), with primary responsibility for implementing the dual graphical user interface (24) being placed upon the client computer (17) (as shown in the example of FIG. 5). As to these embodiments, the client computer (17) can run the dual graphical user interface program (25) implementing a dual graphical user interface (24) to retrieve data (22) from the server computer (18). The dual graphical user interface program (25) can operate to download data (22) from the server computer (18) in a common format for display as the dual graphical user interface (24) on the display surface (3) of the client computer (17).

Now referring primarily to FIG. 5, as an illustrative example, the client computer (17) can include one or more of: a processor unit (26), one or more memory elements (27), and a bus (28) which operably couples components of the client computer (17) including the memory element (27) to the processor unit (26). As to particular embodiments, a first client computer (71) can have a first client computer processor unit (26A) in communication with a first client computer memory element (27A) and a second client computer (72) can have a second client computer processor unit (26B) in communication with a second client computer memory element (27B).

The processor unit (26) can comprise one central-processor unit (CPU), or a plurality of processor units which operate in parallel to process digital information. The bus (28) may be any of several types of bus configurations including a memory bus or memory controller, a peripheral bus, and a local bus using any of a variety of bus architectures. The one or more memory elements (27) can without limitation be a read only memory (ROM) (29), a random access memory (RAM) (30), or both. A basic input/output system (BIOS) (31), containing routines that assist transfer of data (22) between the components of the client computer (17), such as during start-up, can be stored in ROM (29). The client computer (17) can further include a hard disk drive (32) for reading from or writing to a hard disk (33), a magnetic disk drive (34) for reading from or writing to a removable magnetic disk (35), or an optical disk drive (36) for reading from or writing to a removable optical disk (37) such as a CD ROM or other optical media. The hard disk drive (32), magnetic disk drive (34), or optical disk drive (36) can be connected to the bus (28) by a hard disk drive interface (38), a magnetic disk drive interface (39), or an optical disk drive interface (40), respectively. The drives and their associated computer-readable media can provide non-volatile storage of the dual graphical user interface program (25) providing computer-readable instructions, data structures, program modules, or other data for the client computer (17). It can be appreciated by those skilled in the art that any type of computer-readable media that can store data (22) that is accessible by a computer, such as magnetic cassettes, flash memory cards, digital video disks, Bernoulli cartridges, random access memories (RAMs), read only memories (ROMs), or the like, may be used in a variety of operating environments. A number of program modules may be stored on any one or more of the hard disk drive (32), magnetic disk drive (35), optical disk drive (37), ROM (29), or RAM (30), including an operating system (41), one or more application programs (42) including the dual graphical user interface program (25) executable to implement the dual graphical user interface (24) in the form of a first graphical user interface (43) and a second graphical user interface (44), each including one or more graphical user interface images (45).

Again referring primarily to FIG. 5, one or more users (46) can enter commands and information into the client computer (17) through peripheral input devices (47) such as a keyboard (48) or a pointing device (49), such as a mouse (50); however, any method or device that converts user action into commands and information can be utilized including, but not limited to: a microphone, a joystick, a game pad, a touch screen, or the like. A monitor (51) or other type of display device can also be connected to the bus (28) via a video interface (52), such as a video adapter, or the like. The client computer (17) can further include one or more peripheral output devices (53), such as a speaker or a printer; although the peripheral output devices (53) are not so limited.

"User interaction" occurs when the one or more users (46) operates one or more functions of the dual graphical user interface program (25) through the use of a command such as pressing or releasing a left mouse button (54) while a pointer (55) is located over a control icon (56) displayed in a first or second graphical user interface (43)(44). However, it is not intended that "user interaction" be so limited, rather, "user interaction" is intended to broadly encompass a command by the user (46) through which a function of a dual graphical user interface program (25) (or other program, application, module, or the like) is activated whether through selection of one or a plurality of control icons (56), input of data (22) into a data input field (102), touch on the display surface (3), click event by keyboard stroke or mouse button stroke, voice command, or otherwise.

Figure 2:
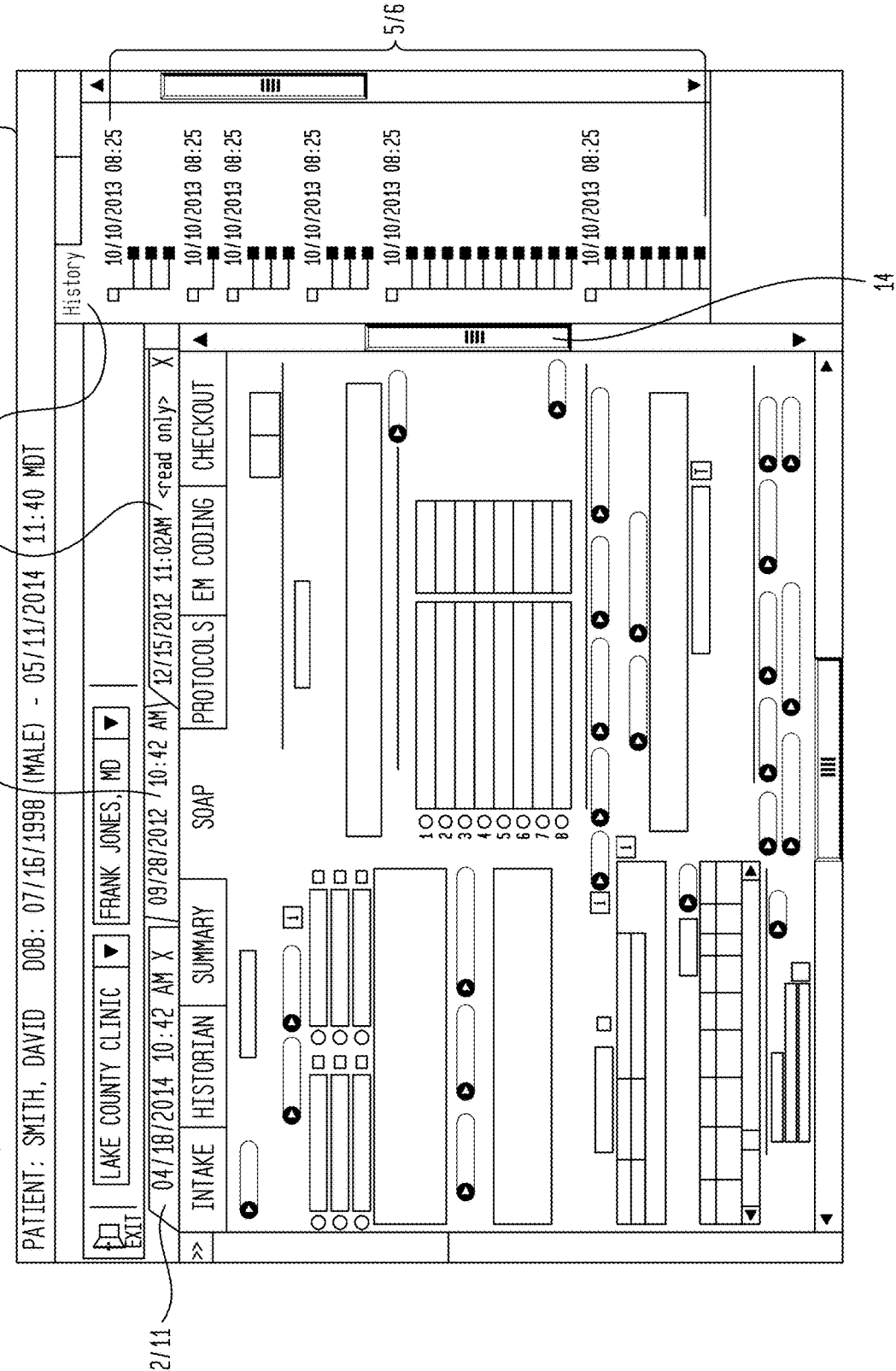
FIG. 2 is an illustrative example of a conventional electronic medical record graphical user interface depicting a first patient history template Sep. 28, 2012 10:42 AM and a second patient history template Dec. 15, 2012 11:02 AM opened in overlaying relation.

Again referring to FIG. 5, the client computer (17) can operate in a networked environment using one or more logical connections (58) to connect to one or more server computers (18). These logical connections (58) are achieved by one or more communication devices (59) coupled to or a part of the client computer (17). The logical connections (58) depicted in FIG. 2 can include a local area network (21) ("LAN") or a wide area network (19) ("WAN"). Such networking environments are commonplace in offices, enterprise-wide computer networks, intranets, wireless networks, global satellite networks, cellular phone networks and the Internet (20).

When used in a LAN-networking environment, the client computer (17) can be connected to a LAN (21) through a local network interface (62), which is one type of communications device (59). When used in a WAN-networking environment, the client computer (17) typically includes a modem (63), another type of communications device (59), or any other type of communications device for establishing communications over the WAN (19), such as the Internet (20). The modem (63), which may be internal or external, can be connected to the bus (28) via a serial port interface (64). It is appreciated that the network connections shown are exemplary and other means of and communications devices (59) for establishing a communications link between one or more client computers (17) and one or more server computers (18) can be used.

Again referring primarily to FIG. 5, which generally illustrates a particular embodiment of a client computer (17) including a display surface (3) capable of displaying the first graphical user interface (43) and the second graphical user interface (44) implemented by execution of the dual graphical user interface program (25) contained in a server memory element (65) of the server computer (18) (as shown in the example of FIG. 4). As to particular embodiments, the display surface (3) can be in the form of one continuous display surface (66) capable of concurrent display of the first graphical user interface (43) in a first image display area (67) and the second graphical user interface (44) in a second image display area (68) (as shown in the example of FIG. 4). As to other embodiments, the client computer (17) can include a first display surface (69) discrete from the second display surface (70) capable of corresponding concurrent display of the first graphical user interface (43) and the second graphical user interface (44) (as shown in the example of FIG. 5). As to other embodiments, the client computer (17) can encompass a first client computer (71) discrete from a second client computer (72) each correspondingly providing the first display surface (69) and the second display surface (70) capable of concurrently displaying the first graphical user interface (43) and the second graphical user interface (44) (also as shown in FIG. 5). As one illustrative example, a client computer (17) can encompass a first tablet computer (73) and a second tablet computer (74) providing the first display surface (69) discrete from the second display surface (70) for corresponding concurrent display of the first graphical user interface (43) and the second graphical user interface (44). While the embodiment of the client computer (17) shown in FIG. 5 includes the computer elements of a conventional desktop or laptop computer, it is not intended that embodiments of the invention include a client computer (17) configured only as a desktop computer or a laptop computer, rather, it is to be understood that the computer elements can be configured in any manner suitable to practice one or more embodiments of the invention. While each of FIG. 6 through FIG. 19 illustrate concurrent display of the first graphical user interface (43) on a first display surface (69) and the second graphical user interface (44) on a second display surface (70), such as first and second display surfaces (69)(70) of first and second tablet computers (73)(74), it is not intended that the concurrent display of the first graphical user interface (43) on a first display surface (69) and the second graphical user interface (44) on a second display surface (70) as shown limit the invention to a particular embodiment or configuration of a display surface (3), a display area (67)(68), or type, kind, or quantity of graphical user interface images (45).

As to particular embodiments, each client computer (17) can use the Internet browser (23) to simply display downloaded content and to relay user inputs (76) back to the server computer (18) (as shown in the example of FIG. 4). A server processor (77) in communication with the server memory element (65) containing the dual graphical user interface program (25) responds by formatting the first graphical user interface (43) and the second graphical user interface (44) and downloading each for display on the corresponding first and second display surfaces (69)(70) (or first and second image display areas (67)(68)) of the client computer (17). The dual graphical user interface program (25) is further executable to populate a plurality of data input fields (102) in the first and second graphical user interfaces (43)(44), as further described below.

Again referring primarily to FIG. 4, the server computer (18) can encompass a plurality of server computers (18) and the dual graphical user interface program (25) can, independently or in association with other programs (80), retrieve from one or a plurality of server computers (18) the electronic medical records (81) or the electronic health records (82) of a corresponding one or a plurality of patients (83). The term electronic medical records (81) refers the legal record of patient encounters and medical services received by one of the plurality of patients (83) from one or more care delivery organizations (85) each in a common format using a common clinical data repository (86). As an illustrative example, a care delivery organization (85) might include a hospital and a clinic owned by the same parent company and using a common format for electronic medical records (81) which are stored in the common clinical data repository (86). The term electronic health records (82) refers to in regard to one of a plurality of patients (83) an accumulation of electronic health records (82) of a plurality of unaffiliated care delivery organizations (88) which in turn utilize unaffiliated clinical data repositories (89) which may not be in a common format. As an illustrative example, electronic health records (82) can be retrieved from the National Health Information Network which is the proposed national repository for electronic health records (82).

The server processor (77) in communication with the server memory element (65) containing the dual graphical user interface program (25) can further function to translate data (22) contained in the electronic medical records (81) and electronic health records (82) retrieved from the server memory element (65), one or more common clinical data repositories (86), or one or more unaffiliated clinical data repositories (89) (or a combination thereof) into a common format which can be downloaded for display in the plurality of data input fields (102) of the first graphical user interface (43) and the second graphical user interface (44) on the corresponding first and second display surfaces (69)(70) (or first or second image display areas (67)(68) depending upon the embodiment) of one or more client computers (17).

Now referring primarily to FIG. 4, as to particular embodiments, the first graphical user interface (43) and the second graphical user interface (44) can be displayed on the display surface (3) of one or more client computers (17) which allows concurrent viewing and interaction by one or more users (46). The dual graphical user interface program (25) can further function to synchronize the data (22) displayed within the plurality of data input fields (102) of the first graphical user interface (43) and the second graphical user interface (44) giving the impression to the user (46) that the first and second graphical user interfaces (43)(44) are directly linked while in actuality each of the first and second graphical user interfaces (43)(44) can operate discretely based on user input (76) relayed back to the server computer (18). The server computer (18) responds by formatting graphical user interface images (45) for the first and second graphical user interfaces (43)(44) in which data (22) is synchronized and downloaded to the client computer (17).

Again referring primarily to FIG. 4, as to particular embodiments, the first graphical user interface (43) and the second graphical user interface (44) can be displayed on a discrete first display surface (69) and second display surface (70) of corresponding first and second client computers (71)(72) which allows concurrent viewing and interaction by the user (46) in each of the first and second graphical user interfaces (43)(44). The first client computer (71) and the second client computer (72) can be configured to wirelessly send and receive communication signals (90) containing data (22) (as shown by FIG. 4 and FIG. 5 by the double headed arrow) independent of the server computer (18).

The first and second client computers (71)(72) can each include a communication controller (91) having a transceiver (92) and associated antenna (93) to send and receive communication signals (90) between the first and second client computers (71)(72). As to particular embodiments, the communication controller (91) can be a BLUETOOTH controller (94) (for example a TEXAS INSTRUMENTS CC2540 BLUETOOTH System-on-Chip including the associated BLUETOOTH transceiver (95) and BLUETOOTH antenna (96). The BLUETOOTH controller (94) can operate a BLUETOOTH protocol V4.0 BLE having an operating frequency of 2.4 GHz ISM. As to particular embodiments, the communication controller (91) can be a WI-FI controller (97) and the associated WI-FI transceiver (98) and WI-FI antenna (99). The communication controller (91) can also be configured to support IOS 6.0 or ANDROID 4.3 or other operating systems.

As to these embodiments, the dual graphical user interface program (25) can be downloaded to one of the first or second client computers (71)(72) configured to wirelessly communicate with the other independent of the server computer (18), the primary responsibility for implementing the dual graphical user interface (24) being placed upon each of the one or more client computers (17) (as shown in the example of FIG. 5). As to these embodiments, each of the one or more client computers (17) can execute the dual graphical user interface program (25) to format and synchronize graphic user interface images (45) for the first and second graphical user interfaces (43)(44) correspondingly depicted on the corresponding first and second display surfaces (69)(70). The first or second client computer (71)(72), or both, can each implement the dual graphical user interface program (25) to retrieve data (22) from the one or more server computers (18) and divide and synchronize the data (22) between the first graphical user interface (43) and the second graphical user interface (44) and populate the respective plurality of data input fields (102).

Now referring primarily to FIG. 6 through FIG. 19, particular embodiments of the dual graphical user interface program (25) can function to download and correspondingly display on a first display surface (69) (or in a first image display area (67)) the first graphical user interface (43) including one or more first graphical user interface images (100) each including one or more data input fields (102) populated by the execution of the dual graphical user interface program (25) with data input elements (101), including, but not necessarily patient data elements, and one or more data input fields (102) which by user interaction allows entry of data input elements (103), including, but not necessarily limited to, patient data input elements.

Concurrently, the dual graphical user interface program (25) can function to download and display a second graphical user interface (44) which provides one or more second graphical user interface images (104) each including one or more data input fields (102) which can be populated by data input elements (101) retrieved from one or more server computers (18) and including data input fields (102) fillable by user interaction with data input elements (103).

With respect to FIG. 6 through FIG. 19, while the first graphical user interface (43) is illustratively displayed to the left of the second graphical user interface (44) in the Figures, understandably, the first graphical user interface (43), the second graphical user interface (44), and the related user interactive features can be displayed in any spatial relationship depending on the configuration of the computer elements. The first and second graphical user interfaces (43)(44) can be displayed in a wide variety of formats depending on the preferences of the designer and the particular efficiencies desired for a given circumstance.

Again referring primarily to FIG. 6 through FIG. 19, the first graphical user interface (43) can include a plurality of first graphical user interface images (100) each selectable for display on the first display surface (69) (or first image display area (67)) by user interaction with a corresponding plurality of first interface index tabs (106) (also referring to as "first data input field identifiers"). As shown in the illustrative example, the plurality of first interface index tabs (106) can include: "inbox tab" (107), "medical history tab" (108), "encounters tab" (109), "demographics tab" (110), "diagnostics tab" (111), and "education tab" (112). Upon user interaction to select one of the plurality of first interface index tabs (106), the dual graphical user interface program (25) functions to display the corresponding one of the plurality of first graphical user interface images (100).

Again referring primarily to FIG. 6 through FIG. 19, the second graphical user interface (44) can include a plurality of second graphical user interface images (104) each selectable for display on the second display surface (70) (or second image display area (68)) by user interaction with a corresponding plurality of second interface index tabs (113) (also referring to as "second data input field identifiers"). As shown in the illustrative example, the plurality of second interface index tabs (113) can include: "inbox tab" (114), "progress note tab" (115), "prescriptions tab" (116), "orders tab" (117), and "favorites tab" (118). Upon user interaction to select one of the plurality of second interface index tabs (113), the dual graphical user interface program (25) functions to display the corresponding one of the plurality of second graphical user interface images (104).

As to particular embodiments, the dual graphical user interface program (25) can further function to couple one each of the plurality of first graphical user interface images (100) with one each of the plurality of second graphical user interface images (104); however, the invention need not be so limited, as a first graphical user interface image (100) can be but is not necessarily coupled with a second graphical user interface image (104), depending upon the application. Accordingly, as to particular embodiments, one each of the plurality of first graphical user interface images (100) can be coupled with one each of the plurality of second graphical user interface images (104). As to other particular embodiments, one each of the plurality of first graphical user interface images (100) can be uncoupled from one each of the plurality of second graphical user interface images (104). As to yet other particular embodiments, one or more first graphical user interface images (100) can be coupled with one or more second graphical user interface images (104) and one or more first graphical user interface images (100) can be uncoupled from one or more second graphical user interface images (104).

Each of the plurality of first graphical user interface images (100) can be coupled with one each of the plurality of second graphical user interface images (104) such that user interaction to select one of the plurality of first or second interface index tabs (106)(113) causes the dual graphical user interface program (25) to concurrently display in the first and second display surfaces (69)(70) (or first and second image display areas (67)(68)) correspondingly coupled first or second graphical user interface images (100)(104). As shown by the illustrative example of FIG. 8, user interaction with the second graphical user interface (44) to select the "progress note tab" (115) in one of the plurality of second graphical user interface images (104) causes execution of the dual graphical user interface program (25) to concurrently depict the coupled one of the plurality of first graphical user interface images (100) associated with the "medical history tab" (108) in the first graphical user interface (43) on the first display surface (69) (or first image display area (67)).

Similarly, user interaction in the first graphic user interface (43) to select the "medical history tab" (108) in the first graphic user interface (43) depicted on the first display surface (69) (or in the first image display area (67)) can cause concurrent depiction of the "progress note tab" (115) in the second graphical user interface (44) on the second display surface (70) (or in the second image display area (68)).

Now referring primarily to FIG. 6 through FIG. 19 which illustrate a particular embodiment of a plurality of first graphical user interface images (100) and a plurality of second graphical user interface images (104) displayed on corresponding discrete first and second display surfaces (69)(70) (or first and second image display areas (67)(68)) by computer implemented execution of an embodiment of the dual graphical user interface program (25).

Now referring primarily to FIG. 6 which illustrates a first of the plurality of first and second graphical user interface images (100)(104) correspondingly displayed in the first and second graphical user interfaces (43)(44) including a login field (119) displayed in the second graphical user interface (44) which by user interaction allows user login to the dual graphical user interface program (25) and access to the inventive dual interface electronic medical records management system (16) (as shown in the example of FIG. 4 and FIG. 5). The user login elements can include conventional two factor credentials (username and password) which authenticated allows the user (46) access to the dual interface electronic medical records management system (16) including in part the dual graphical user interface program (25). As to particular embodiments, a fingerprint reader (120), whether integral or discrete from the first or second display surface (69)(70), can be used to scan a fingerprint image (121) of the user (46) to authenticate the user (46). Fingerprint identification by user interaction with the first or second graphical user interface (43)(44) provides an advantage by avoiding use of conventional two factor credentials which may in conventional electronic medical records graphical user interfaces (1) may have to be entered multiple times to access the conventional electronic medical records graphical user interfaces (1). Upon successful login by user interaction, the dual graphical user interface program (25) can function to default to a second of the plurality of graphical user interface images (104) in each of the first and second graphical user interfaces (43)(44) and as to particular embodiments, can as a default display a first and second inbox interface images (122)(123) correspondingly associated with the first and second graphical user interface "inbox tabs" (107)(114).

Now referring primarily to FIG. 7, the first inbox interface image (122) depicted in the first graphical user interface (43) includes a task list (124) of tasks (125) including but not limited to: phone calls; refill orders for prescriptions; and any of a number of other clinical tasks forwarded to the user (46). Once a task (125) has been completed, the user (46) may either: (a) delete it or (b) flag it with descriptive reminders, such as "further follow up needed." The dual graphical user interface program (25) can further function to depict in the first inbox interface image (122) (or other interface image) a meaningful use report card image (126) which by user interaction can be opened to depict a meaningful use report (127) showing percentage of compliance of care objectives, menu set objectives, and clinical quality measures that have been successfully reported to Centers for Medicare and Medicaid Services Incentive program.

The second inbox interface image (123) depicted in the second graphical user interface (44)) includes a "patient schedule image" (128) including a schedule of patients (129) associated with a schedule date (130) and schedule time (131). By user interaction in the second inbox interface image (123), a patient identifier (132) can be selected to retrieve the electronic medical record (81) (or combined electronic medical and health record (81)(82)) associated with a patient identifier (132). Upon selection of a patient identifier (132), the dual graphical user interface (24) functions to populate the data input fields (102) of each of the plurality of first graphical user interface images (100) and the plurality of second graphical user interface images (104) with data (22) related to the selected one patient identifier (132).

Now referring primarily to FIG. 8 which illustrates a third of the plurality of first graphical user interface images (100) and a third of the plurality of second graphical user interface images (104) displayed upon user interaction to select a patient identifier (132) from the schedule of patients (129) or from another form of patient identifier selector such as a drop down list of patient identifiers (132). In this example, a progress note interface image (134) can be displayed in the second graphical user interface (44) and by operation of the dual graphical user interface (24), a coupled medical history interface image (135) can be displayed in the first graphical user interface (43). User (46) can enter data input elements (103) into the data input fields (102) of the progress note interface image (134) while concurrently viewing the medical history interface image (135) of the first graphical user interface (43). After inputting data into the data input fields (102) of the progress note interface image (134) of the second graphical user interface (44), by user interaction an electronic signature (136) can be entered in the electronic signature field (137) and by user interaction with a submit control icon (138) the progress note interface image (134) can become a permanent addition to the electronic medical record (81) associated with the patient identifier (132) which can then be immediately displayed in the medical history interface image (135) of the first graphical user interface (43).

Now referring primarily to FIG. 9, certain of the plurality of first graphical user interface images (100) can be selected to remain uncoupled from the progress note interface image (134) depicted in the second graphical user interface (44). User interaction with one or more of the first interface index tabs (106) associated with the plurality of first graphical user interface images (100) which are not coupled to the progress note interface image (134), causes the dual graphical user interface program (25) to depict in the first display surface (69) (or first image display area (67)) a first graphical user interface image (100) associated with the selected one of the first interface index tabs (106) while concurrently depicting the progress note interface image (134) on the second display surface (70).

Figure 11:
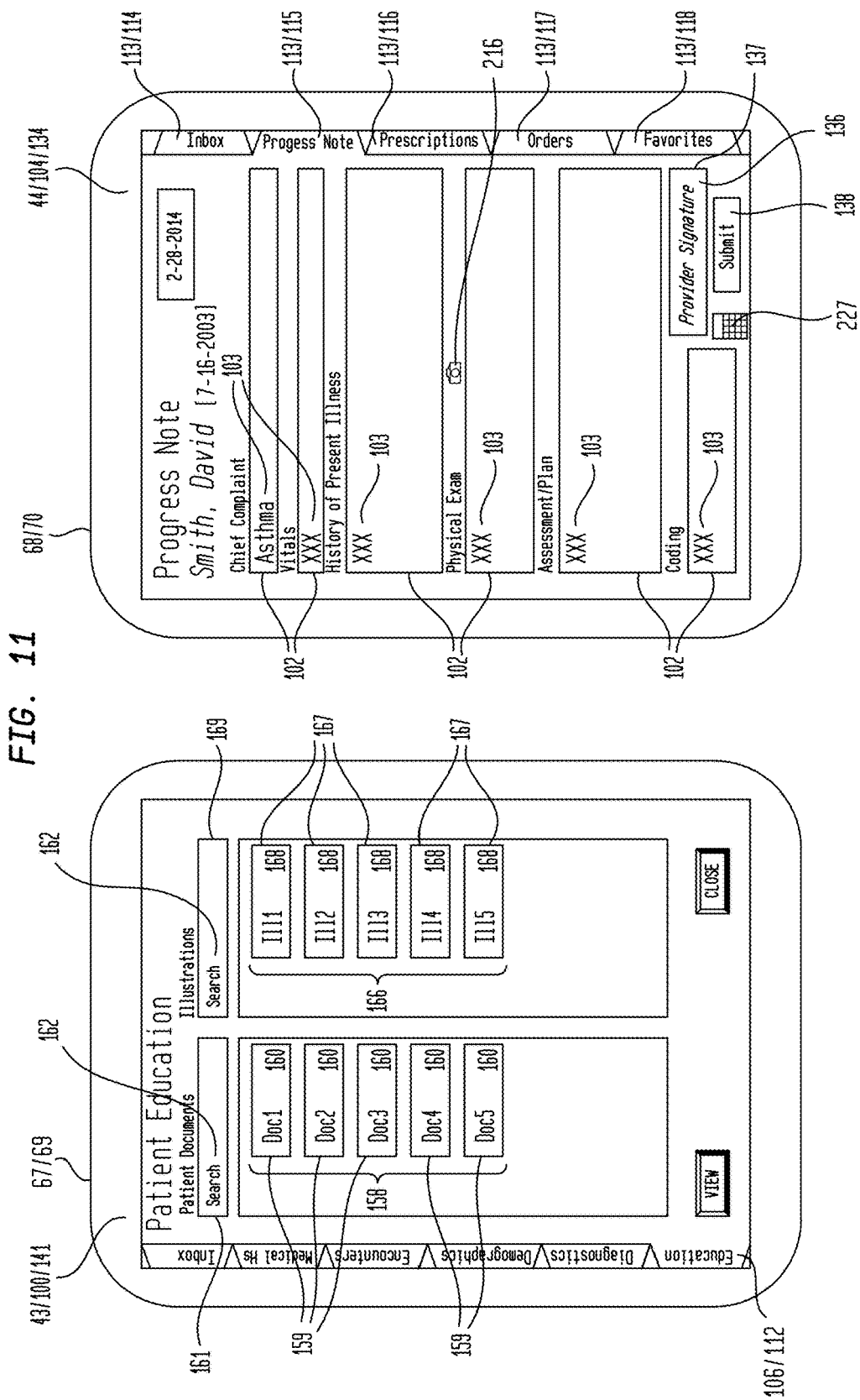
FIG. 11 is an illustration of a particular embodiment of a first graphical user interface image and a second graphical user interface image displayed on corresponding discrete first and second display surfaces by execution of an inventive dual graphical user interface program.

As shown in the illustrative examples of FIG. 9 through FIG. 11, the encounters tab (109), the demographics tab (110), and the education tab (112), selectable in the first graphical user interface (43), and correspondingly associated with an encounters interface image (139), a demographics interface image (140), and a patient education interface image (141) can remain uncoupled from the progress note interface image (134) depicted in the second graphic user interface (44).

Now referring primarily to FIG. 9, by user interaction, the user (46) can select the encounters tab (109) to cause the dual graphical user interface program (25) to depict the encounters interface image (139) on the first display surface (69). The encounters interface image (139) can include archival progress notes (142) in reverse chronological order. The user (46) can scroll through the archival progress notes (142) which by user interaction with a scroll control icon (143), shown in the example of FIG. 9 as a pair of page turning arrows (144). Embodiments of the encounters interface image (139) can further include an encounters drop down list which by user interaction causes the dual graphical user interface program (25) to retrieve data (22) from one or more encounter categories such as: consults, emergent care visits, operative reports, telephone calls, or the like.

Now referring primarily to FIG. 10, by user interaction, the user (46) can select the demographics tab (110) to cause the dual graphical user interface program (25) to depict a demographics interface image (140) on the first display surface (69). The demographics interface image (140) can include demographic data (147) associated with the selected patient identifier (132) such as family information (148) including residence address (149), telephone number (150), social history (151), family history (152), insurance data (153), and pharmacy (154). Particular embodiments of the demographics interface image (140) can further include a patient identifier communication control icon (155) which by user interaction causes the dual graphical user interface program (25) to retrieve the telephone number (150) (or other communication identification information) associated with the patient identifier (132) and further functions to configure the first or second client computer (71)(72) as a client computer communication device (156) (or e-mail, text messaging, or other communication configuration device) which connects with a communication device (157) discrete from the first or second client computer (71)(72), the communication device (157) associated with the selected patient identifier (132). Accordingly, the user (46) can have voice communication (or text, e-mail, or other type communication) with the one of the plurality of patients (83) associated with the selected patient identifier (132) while concurrently entering data input elements (103) into the progress note interface image (134) depicted in the second graphical user interface image (104). Additionally, by user interaction with the second interface index tabs (113), the user (46) can during voice communication with the patient (83) access any second graphical user interface images (104) containing data (22) associated with the patient identifier (132) whether coupled or uncoupled from the progress note image interface (134) which allows user interaction to fill data input elements (103) into data input fields (102) of the progress note interface image (134).

Now referring to FIG. 11, by user interaction, the user (46) can select the patient education tab (112) to cause the dual graphical user interface program (25) to depict a patient education interface image (141) on the first display surface (69). In the example of FIG. 11, the patient education interface image (141) includes a patient education document list (158) including a plurality of patient education document selection elements (159) each selectable by user interaction to cause the dual graphical user interface program (25) to depict the selected one patient education document (160) on the first display surface (69). A patient education document search field (161) can be further included in the patient education interface image (141) which allows the user (46) to enter a search element (162) causing the dual graphical user interface program (25) to search a patient education document database (163) contained in the server memory element (65) for patient education document files (164) associated with the entered search element (162) and those patient education document files (164) associated with the search element (162) can be returned and depicted as a patient education document list (158) including patient education document selection elements (159) selectable by the user (46) to view a patient education document (160) on the first display surface (69).

As to particular embodiments, the patient education interface image (141) can further include a patient education illustrations list (166) including a plurality of patient education illustration selection elements (167) each selectable by user interaction to cause the dual graphical user interface program (25) to depict the selected one patient education illustration (168) on the first display surface (69). A patient education illustration search field (169) can be further included in the patient education interface image (141) which allows the user (46) to enter a search element (162) causing the dual graphical user interface program (25) to search a patient education illustrations database (170) contained in the server memory element (65) for patient education illustration files (171) associated with the entered search element (162) and those patient education illustration files (171) associated with the search element (162) can be returned and depicted as a patient education illustrations list (166) including the plurality of patient education illustration selection elements (167) selectable by the user (46) to view the patient education illustration (168) on the first display surface (69).

An advantage afforded by the dual graphical user interface (24) can be that the patient education interface image (141) being uncoupled from the second graphical user interface (44) allows a second user (172) to interact in the first graphical user interface (43) depicted on the first display surface (69) discrete from a first user (173) interacting with the second graphical user interface (44) depicted on the second display surface (70). Accordingly, both the first and the second users (173)(172) can independently interact with the first and second graphical user interfaces (43)(44) giving each of the first and second users (173)(172) the impression that the first and second display surfaces (69)(70) are wholly disconnected, even though the dual graphical user interface (24) maintains connectivity and interoperability of the first and second graphical user interfaces (43)(44), as above described.

Figure 12:
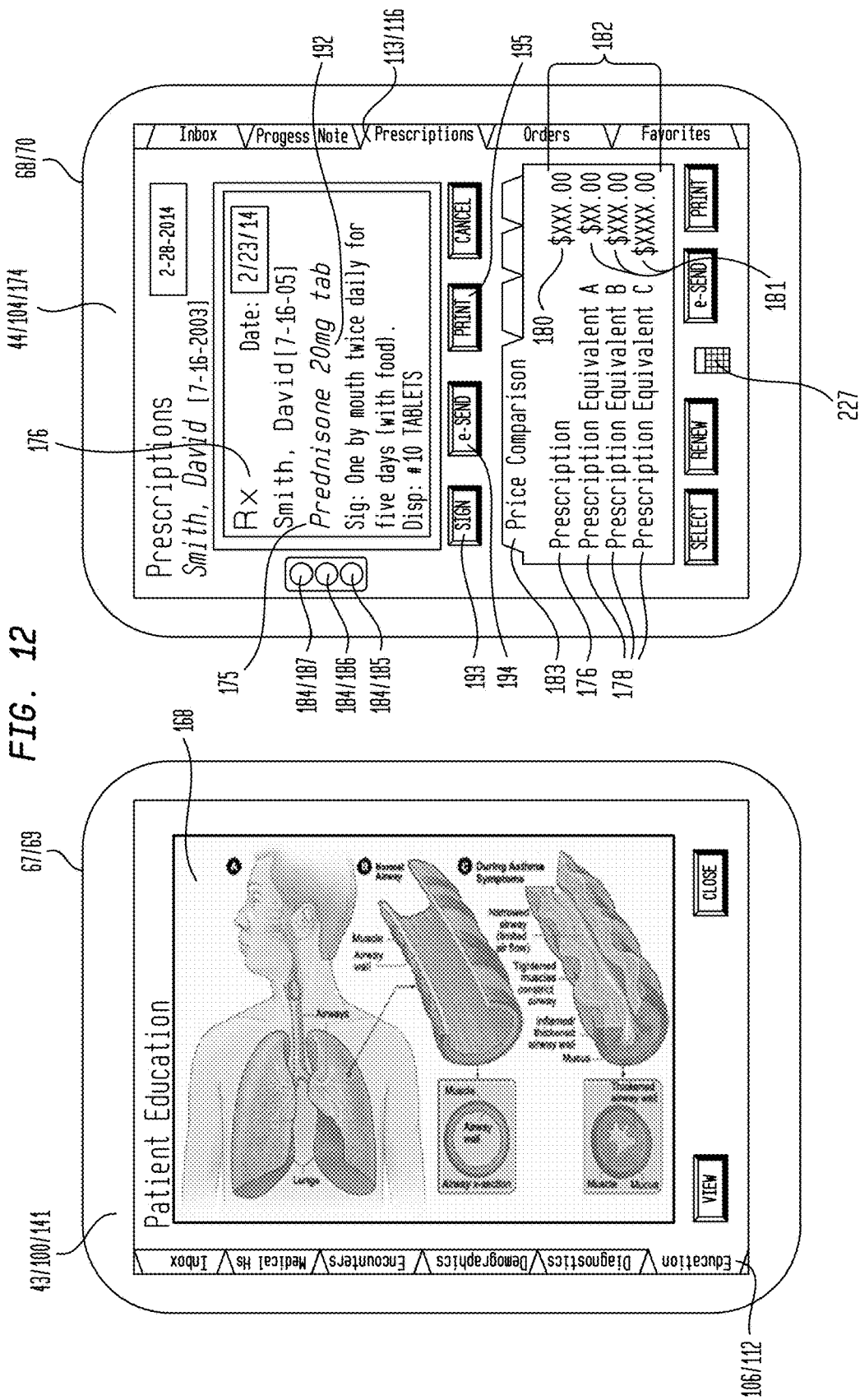
FIG. 12 is an illustration of a particular embodiment of a first graphical user interface image and a second graphical user interface image displayed on corresponding discrete first and second display surfaces by execution of an inventive dual graphical user interface program.

Now referring to the illustrative example of FIG. 12, as an illustrative example, the second user (172) can by user interaction in the patient education interface image (141) display a patient education illustration (168) relating to asthma entirely independent of the first user (173) which by user interaction with the prescriptions tab (116) of the second graphical user interface (44) has caused the graphical user interface program (25) to depict a prescriptions graphical user interface image (174) on the second display surface (70). The prescriptions graphical user interface image (174) can include one or more data input fields (102) which by user interaction, whether by a drop down list of medications (175), by keystroke on a keyboard (48), or otherwise, can be filled with a prescription (176) for a medication (175).

As to particular embodiments, the entry of a prescription (176) for a medication (175) in the data input field (102) can cause the dual graphical user interface program (25) to compare the prescription (176) entered to prescription equivalents (178) contained in a prescription database (179) of the server memory element (65) and return the prescription (176) with a prescription price (180) and return prescription equivalents (178) with prescription equivalent prices (181) as a prescription pricing comparison list (182) depicted in the prescription graphical user interface image (174) on the second display surface (70). As shown in the example of FIG. 12, the prescription pricing comparison list (182) can be accessed by user interaction with a price comparison tab (183) included in the prescription graphical user interface image (174). As to particular embodiments, the prescription graphical user interface image (174) can further include sensorially perceivable prescription price comparison indicia (184). In the illustrative example of FIG. 12, the dual graphical user interface program (25) depicts sensorially perceivable prescription price comparison indicia (184) as a green indicator (185), a yellow indicator (186), and a red indicator (187) which the dual graphical user interface program (25) illuminates in the alternative based on comparison of the prescription price (180) against prescription equivalent prices (181), as above described. For example, if based on comparison of the prescription price (180) against the prescription equivalent prices (181), the prescription price (180) is lower or equivalent to the prescription equivalent prices (181), the green indicator (185) illuminates; if the prescription price (180) is intermediate in the range of the prescription equivalent prices (181), the yellow indicator (186) illuminates; and if the prescription price (180) is greater than all or substantially all of the prescription equivalent prices (181), the red indicator (187) illuminates.

Figure 13:
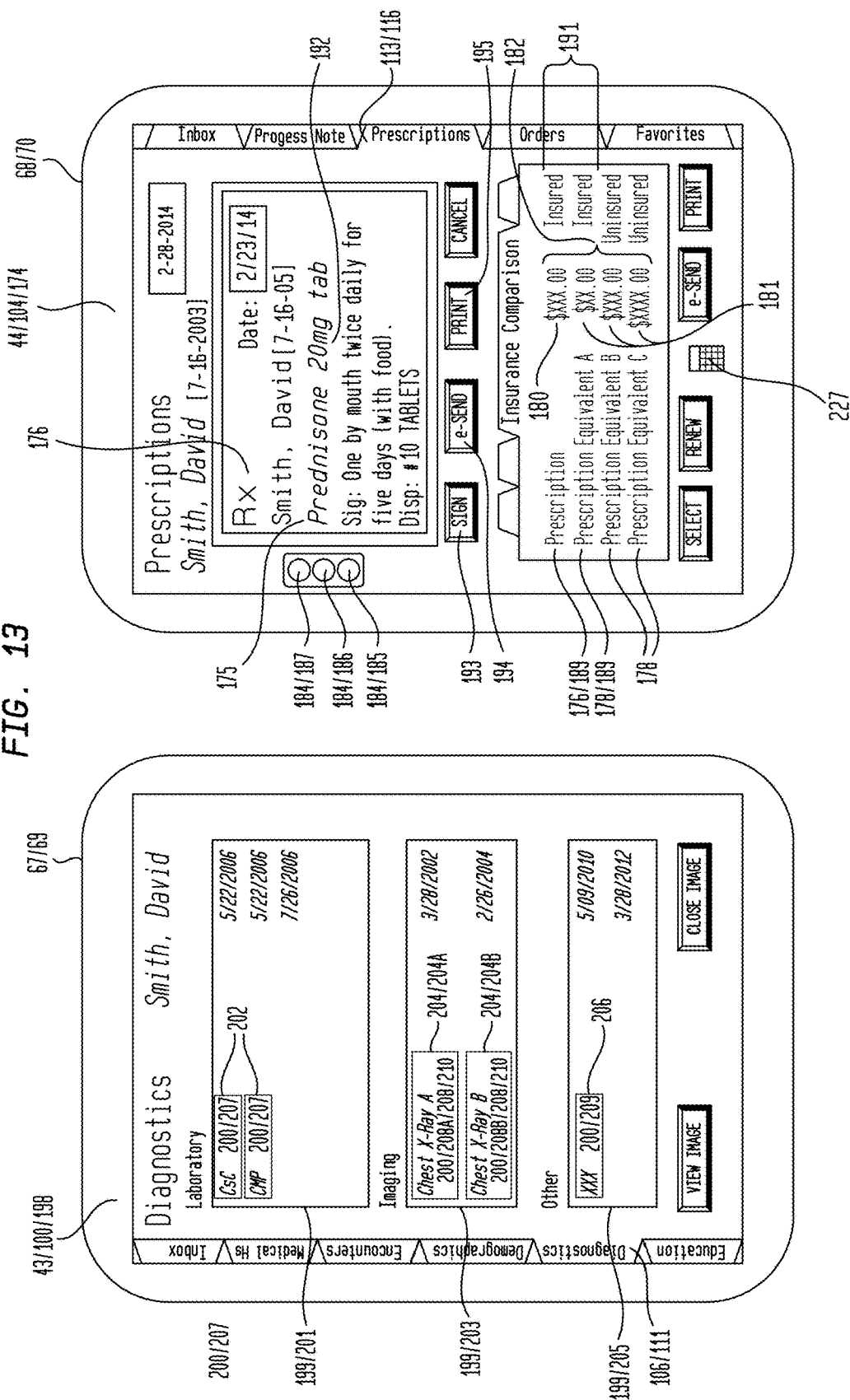
FIG. 13 is an illustration of a particular embodiment of a first graphical user interface image and a second graphical user interface image displayed on corresponding discrete first and second display surfaces by execution of an inventive dual graphical user interface program.

As to particular embodiments, the dual graphical user interface (24) can further compare the prescription (176) and returned prescription equivalents (178) against an insured prescriptions database (188) containing insured prescriptions (189) based on insurance data (190) prior entered into the electronic medical record (81) of the patient (46) associated with the patient identifier (132). As to particular embodiments, the dual graphical user interface (24) can function to depict an insured prescriptions list (191) in the prescription graphical user interface image (174) on the second display surface (70) (as shown in the example of FIG. 13). Accordingly, even if the prescription (176) has the lowest pricing, but is not an insured prescription (189), the first user (173) can change the prescription (176) in the data input field (102) to an insured prescription (189). As to particular embodiments, the dual graphical user interface program (25) can function to provide sensorially perceivable prescription price comparison indicia (184) further based upon whether the prescription (176) is an insured prescription (189). For example, if the prescription (176) is not an insured prescription (189), the red indicator (187) illuminates; if the prescription (176) is an insured prescription (189) having the lowest price compared with the prescription equivalent prices (181), the green indicator (185) illuminates; and if the prescription (176) is an insured prescription (189) having a prescription price (180) intermediate within the range of the prescription equivalent prices (181), then the yellow indicator (186) illuminates.

Again referring primarily to FIG. 12, the prescription (176) including the medication (175) and a dosage (192) can by user interaction be validated by an electronic signature (136) by user interaction with an electronic signature control icon (193) (shown in the example as a "sign" control icon) which by user interaction enters the electronic signature (136) of the first user (173). Additionally, the prescription (176) can be sent directly to the pharmacy (154) associated with the patient identifier (132) by user interaction with a pharmacy control element (194) (shown in the example as an "e-send" icon), or user interaction with a printer control element (195) (shown in the example as a "print" icon) to give a printed prescription to the patient (83). Importantly, when a prescription (176) is validated with the electronic signature (136) of the first user (173), it can be immediately archived as part of the electronic medical record (81) associated with the patient identifier (132), and can be automatically populated, and as to particular embodiments highlighted, in a medication data field (197) of the medical history interface image (135) of the second graphical user interface (44) (as shown in the example of FIG. 14).

Now referring primarily to FIG. 13, a first user (173) can by user interaction in the diagnostics tab (111) of the first graphical user interface (43) cause to be displayed in the first graphical user interface (43) a diagnostics graphical user interface image (198). A diagnostics graphical user interface image (198) can be uncoupled from the second graphical user interface (44) allowing the first graphical user interface (43) to be utilized by the first or second user (173)(172) independent of the second graphical user interface (44). Accordingly, the first user (173) can continue to interact with the second graphical user interface (44) while the second user (172) can continue to interact with the first graphical user interface (43) while the dual graphical user interface (24) maintains connectivity between the first and second graphical user interfaces (43)(44), as above described.

The diagnostics graphical user interface image (198) can include one or more diagnostic fields (199) populated by the dual graphical user interface program (25) with patient diagnostic data (200) retrieved from the electronic medical record (81) associated with the patient identifier (132). As shown in the illustrative example of FIG. 13, the patient diagnostic data (200) can be parsed and depicted in a laboratory diagnostic data field (201) containing selectable patient laboratory diagnostic elements (202), an imaging diagnostic data field (203) containing selectable patient imaging diagnostic elements (204), and a miscellaneous diagnostic data field (205) containing selectable patient miscellaneous diagnostic elements (206). A user (46) can by user interaction with a patient laboratory diagnostic element (202), a patient imaging diagnostic element (204), or a patient miscellaneous diagnostic element (206) cause the dual graphical user interface (24) to retrieve the associated laboratory diagnostic data (207) (for example, a laboratory test report, or the like associated with the laboratory diagnostic element (202)), imaging diagnostic data (208) (for example, a x-ray image, computerized tomography scan image, magnet resonance image, or the like, associated with the imaging diagnostic element (204)), or miscellaneous diagnostic data (209) (for example, patient spirometry data, tuberculosis skin test data, or the like, associated with the miscellaneous diagnostic element (206)).

Figure 14:
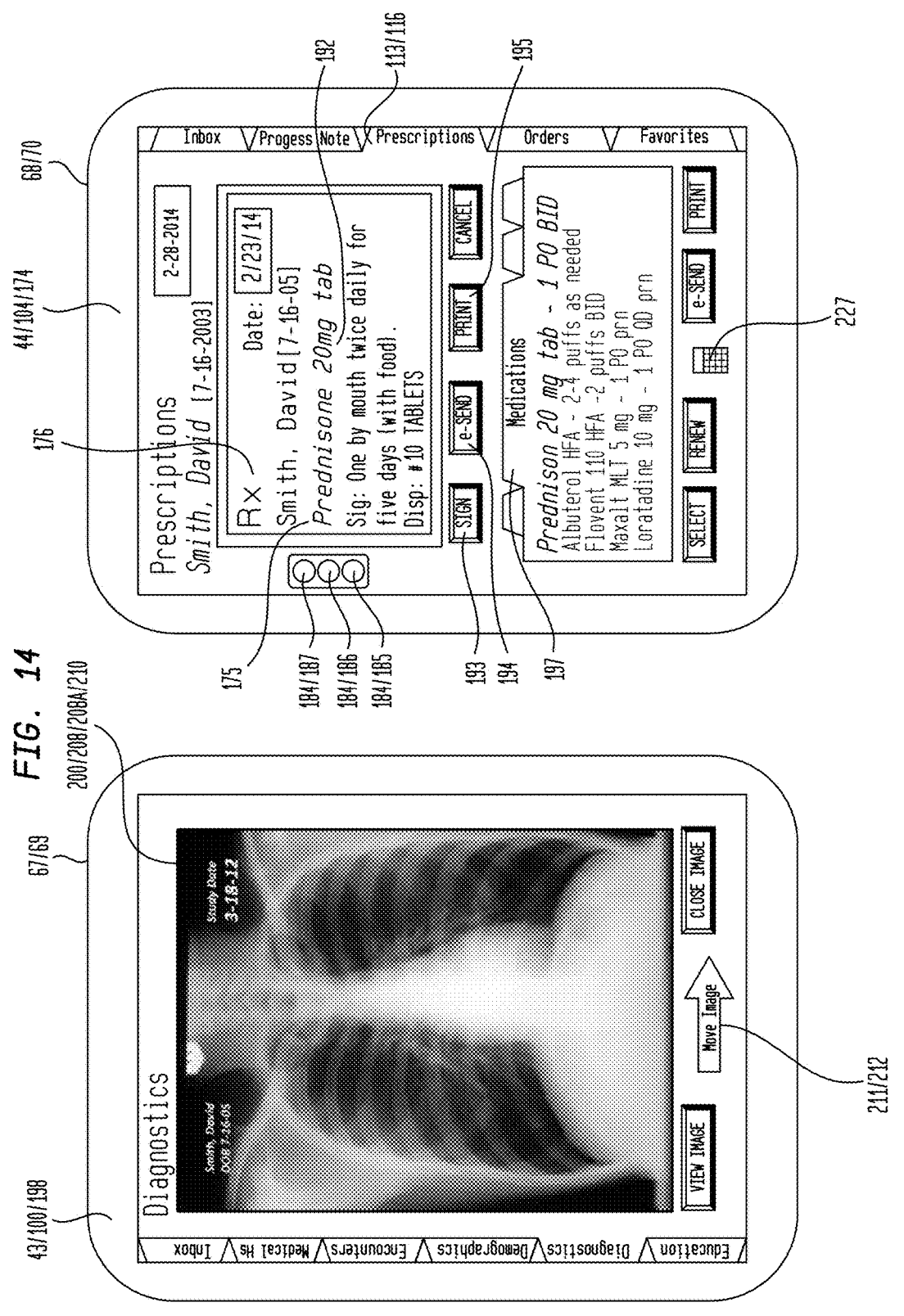

Now referring primarily to FIG. 14, as an illustrative example, the first user (173) by interaction with a first imaging diagnostic element (204A) depicted in the diagnostics graphical user interface image (198) can cause the dual graphical user interface program (25) to retrieve the associated first diagnostic data (208A) in the form of a chest x-ray (210) and depict the chest x-ray (210) in the first graphical user interface (43) on the first display surface (69) which can then be viewed by a second user (172) independent of the first graphical user interface (43) depicted on the second display surface (70).

Figure 15:
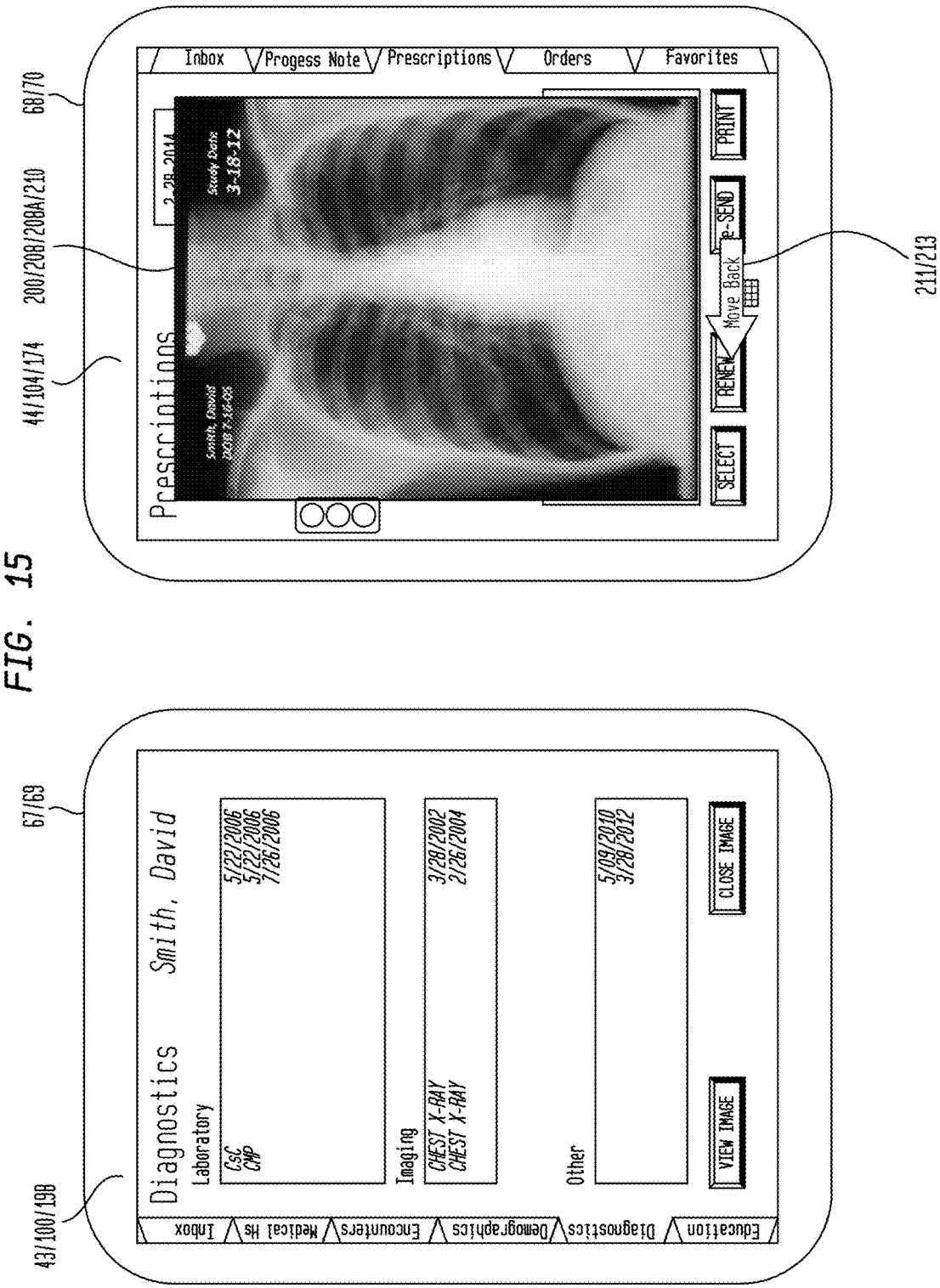
FIG. 15 is an illustration of a particular embodiment of a first graphical user interface image and a second graphical user interface image displayed on corresponding discrete first and second display surfaces by execution of an inventive dual graphical user interface program.

Now referring primarily to FIG. 14 and FIG. 15, as to particular embodiments, the first user (173) and the second user (172) can cause the dual graphical user interface (24) to reciprocally pass the chest x-ray (210) (or other laboratory, imaging, or miscellaneous diagnostic data (207)(208)(209)) between the first graphical user interface (43) and the second graphical user interface (44), thereby allowing the first and second users (173)(172) to independently view the diagnostic data (207)(208)(209) in either the first or second graphical user interface (43)(44). In the example of FIG. 14 and FIG. 15, a diagnostic image movement control icon (211) (shown in the example as first and second directional arrows (212)(213)) can by user interaction with the first or second user (173)(172) cause the chest x-ray (210) (or other patient laboratory, imaging, or miscellaneous diagnostic data (207)(208)(209)) to be reciprocally passed between the first graphical user interface (43) and the second graphical user interface (44).

Figure 16:
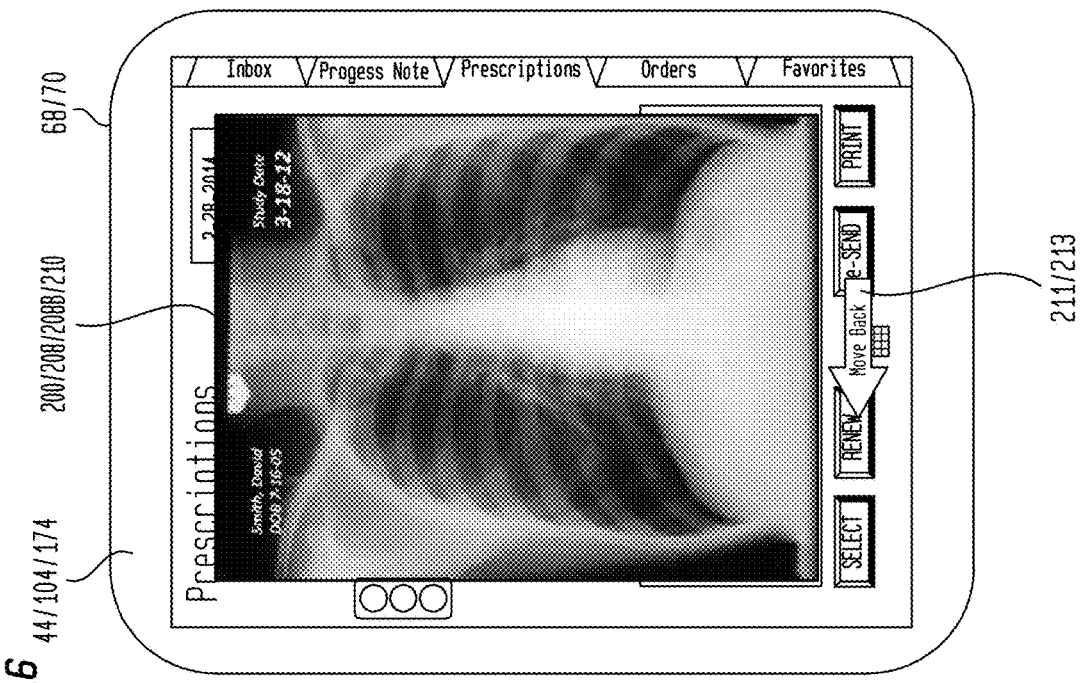
FIG. 16 is an illustration of a particular embodiment of a first graphical user interface image and a second graphical user interface image displayed on corresponding discrete first and second display surfaces by execution of an inventive dual graphical user interface program.

Now referring primarily to FIG. 15 and FIG. 16, once the diagnostic data (207)(208)(209) has been passed from the first graphical user interface (43) to the second graphical user interface (44), the first or the second user (173)(172) can by user interaction select a second imaging diagnostic element (204B) (or other laboratory, imaging, or miscellaneous diagnostic elements (202)(204)(206)) depicted in the diagnostics graphical user interface image (198) in the first graphical user interface (43) causing the dual graphical user interface (24) to retrieve and display the associated second imaging diagnostic data (208B) (or other laboratory, imaging, or miscellaneous diagnostic data (207)(208)(209)) in the first graphical user interface (43), as shown in the example of FIG. 16. This affords the first user (173) and the second user (172) to independently view the first and second imaging diagnostic data (208A)(208B) (or other laboratory, imaging, or miscellaneous diagnostic data (207)(208)(209)) or concurrently view the first and second imaging diagnostic data (208A)(208B) side by side as shown in the example of FIG. 16, or reciprocally pass the first or second imaging diagnostic data (208A)(208B) between the first and the second graphical user interfaces (43)(44).

Now referring primarily to FIG. 17, the first user (173) by user interaction with the progress note tab (115) in the second graphical user interface (44) can return to the configuration of the dual graphical user interface (24) shown in FIG. 8. By further user interaction with an image capture control icon (216) in the progress note interface image (134), the dual graphical user interface (24) can function to configure the second client computer (72) as a client computer image capture device (217) and wirelessly connect the first client computer (71) to the second client computer (72) to receive and display images (218) captured by the second client computer (72) on the first display surface (69) of the first client computer (71). The dual graphical user interface program (25) saves the images (218) captured by the second client computer (72) in the electronic medical record (81) associated with the patient identifier (132) which image (218) can be immediately depicted as an imaging diagnostic element (204) in the diagnostics graphical user interface image (198) and retrieved for display and reciprocal passing, as above described.

As to particular embodiments, the dual graphical user interface program (25) can further depict a ruler control icon (220) which by user interaction causes depiction of a ruler element (221) in the image displayed on the first display surface (69) of the first client computer (71) which by user interaction can be moved within the image (218) and dimension extension lines (222) positioned in relation to an image element (223) in the image (218) and a numerical dimension element (224) selected by user interaction with a drop down dimensions list (225) or fillable user input dimensions fields (226) can be disposed between the dimension extension lines (222).

Figure 19:
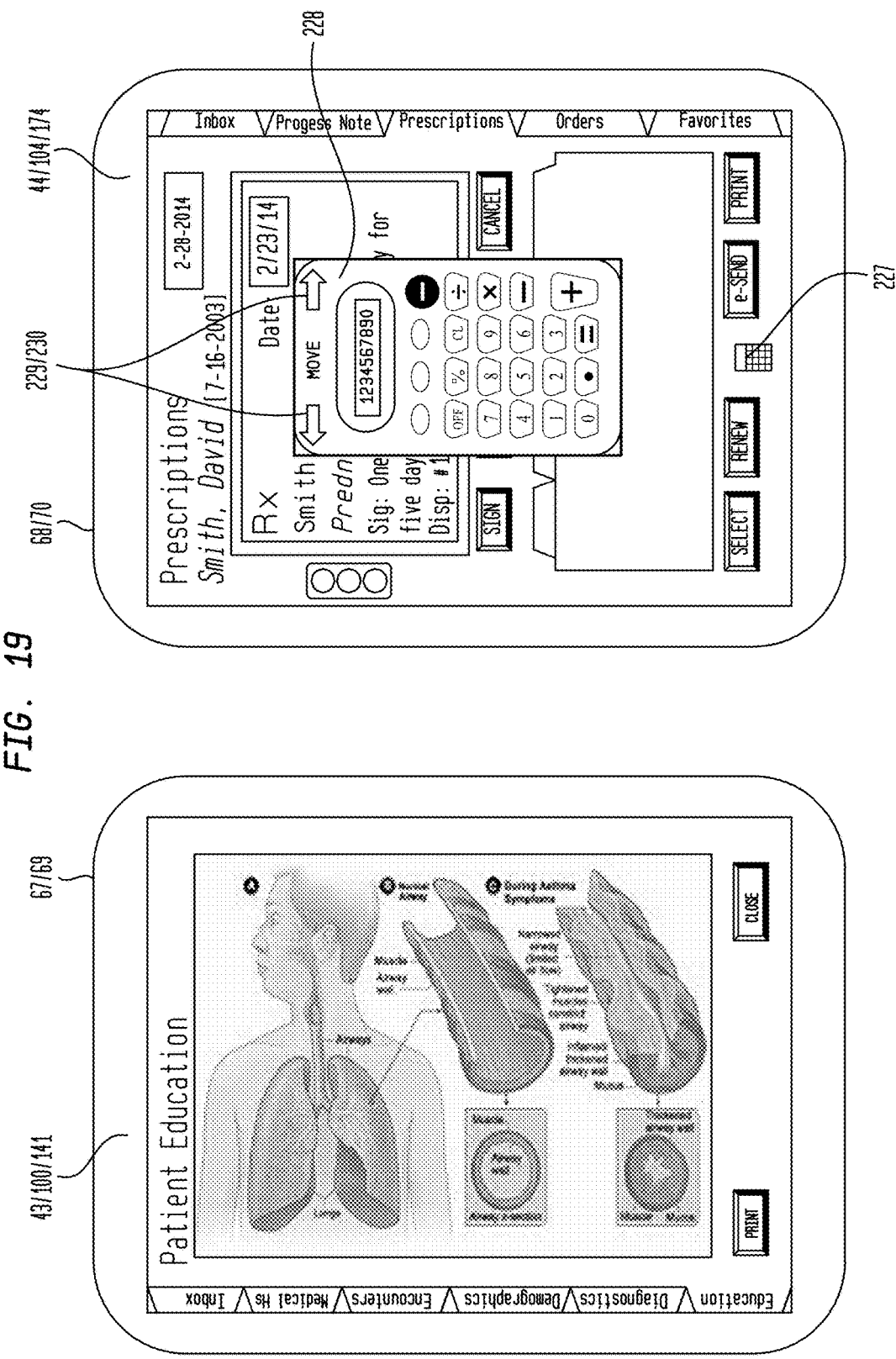
FIG. 19 is an illustration of a particular embodiment of a first graphical user interface image and a second graphical user interface image displayed on corresponding discrete first and second display surfaces by execution of an inventive dual graphical user interface program.
Figure 20:
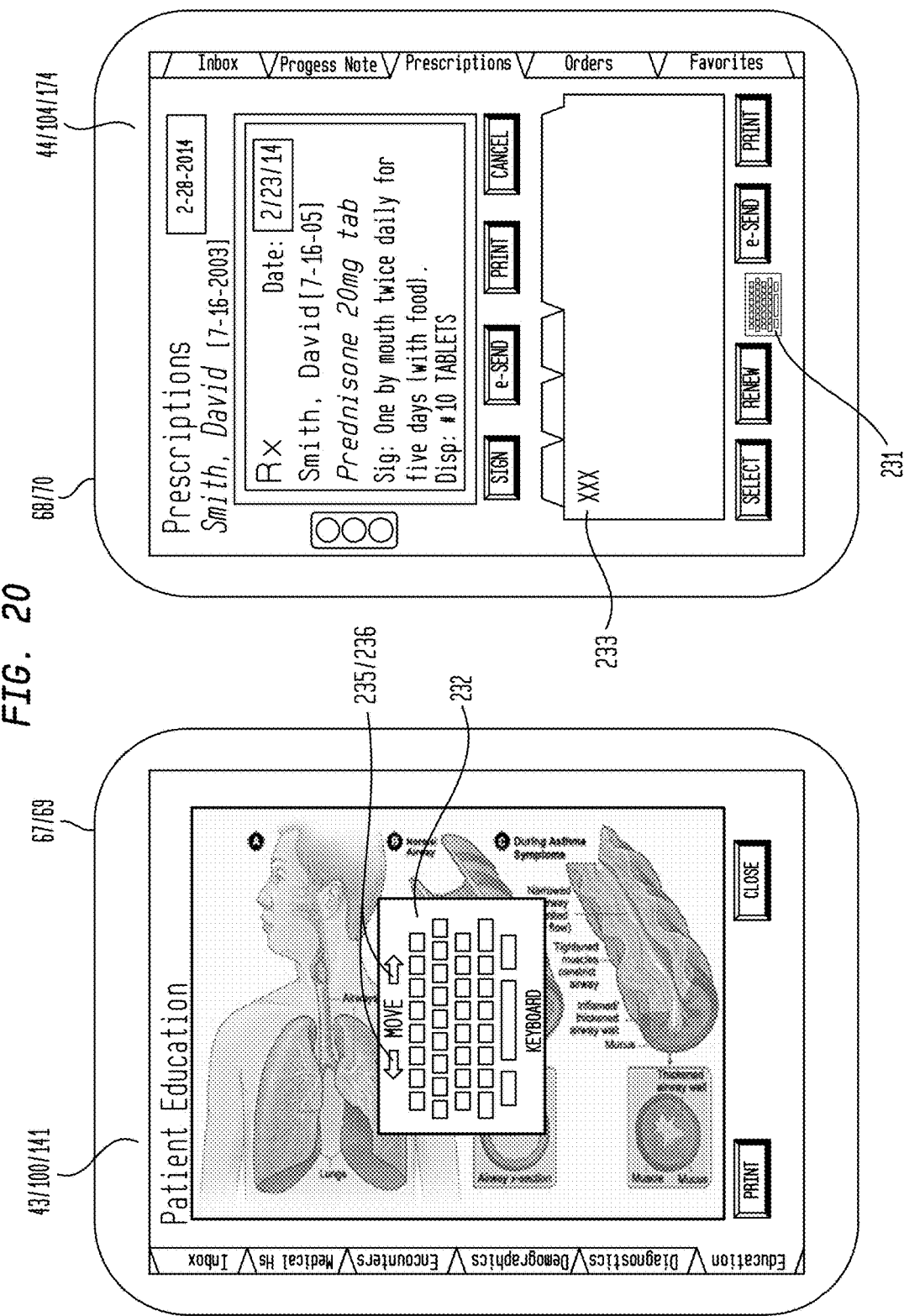
FIG. 20 is an illustration of a particular embodiment of a first graphical user interface image and a second graphical user interface image displayed on corresponding discrete first and second display surfaces by execution of an inventive dual graphical user interface program.

Now referring primarily to FIG. 18 and FIG. 19, the dual graphical user interface (24) can further function to provide a calculator control icon (227) in the second graphical user interface image (104) which by user interaction can cause depiction of a calculator image (228) in the first graphical user interface image (100) which allows continued user interaction in the second graphical user interface image (104) while by user interaction with the calculator image (228) in the first graphical user interface (100) calculations can be performed by the dual graphical user interface program (25), as shown in the example of FIG. 18. As to particular embodiments, the calculator image (228) can be reciprocally passed between the first graphical user interface (43) and the second graphical user interface (44) by user interaction with a calculator movement control icon (229) (shown as arrows (230) in the example of FIG. 18 and FIG. 19).

Again referring primarily to FIG. 18 and FIG. 19, the dual graphical user interface (24) can further function to provide a keyboard control icon (231) in the second graphical user interface image (104) which by user interaction can cause depiction of a keyboard image (232) in the first graphical user interface image (100) which allows continued user interaction in the second graphical user interface image (104) while by user interaction with the keyboard image (232) in the first graphical user interface (43) keystrokes can be performed to enter corresponding keystroke characters (233) into the finable data input fields (102) depicted in the first and second graphical user interfaces (43)(44) by operation of a word processing application (234) of the dual graphical user interface program (25). As to particular embodiments, the keyboard image (232) can be reciprocally passed between the first graphical user interface (43) and the second graphical user interface (44) by user interaction with a keyboard movement control icon (235) (shown as arrows (236) in the example of FIG. 18 and FIG. 19).

As to particular embodiments, the first and the second client computers (71)(72) can be rotated clockwise or counterclockwise with corresponding rotation of the first or second graphical user interfaces (43)(44).

The dual graphical user interface program (25) can have utility in many other applications other than the intake and recording of electronic medical records (81) or electronic health records (82), as described herein, that relate to the "charting" of "subject" material, including but not limited to: charting of dental records; charting of veterinary records; recording of compound performance in pharmaceutical drug trials; repair and maintenance records of fleet vehicles (autos, airplanes, military vehicles); research and recording activities engaged in by criminal justice department (such as criminal booking and intake, parole records) and military intelligence; tracking of students in the educational field (where grades, immunizations, disciplinary actions, educational plans, all "follow" students from year-to-year and grade-to-grade); commercial building and facility maintenance records; and required and/or ongoing environmental reporting (such as emissions of pollutants or production of end-product) in energy-related facilities, plants, and mines, or the like or combinations thereof.

As can be easily understood from the foregoing, the basic concepts of the present invention may be embodied in a variety of ways. The invention involves numerous and varied embodiments of hardware elements, network elements, computer readable media, and a computer code including the best mode of combining the hardware elements, network elements, and computer readable media to afford the inventive dual interface system and a dual graphical user interface and methods of making a dual interface system and using a dual graphical user interface.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of "computer" should be understood to encompass disclosure of the act of "computing"—whether explicitly discussed or not—and, conversely, were there effectively disclosure of the act of "computing", such a disclosure should be understood to encompass disclosure of "a computer" and even a "means for computing." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment.

Thus the applicant(s) should be understood to claim at least: i) dual interface and dual interface system as herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this international PCT patent specification are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice versa as necessary to define the matter for which protection is sought by this application or by any subsequent application or continuation, division, or continuation in part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation in part application thereof or any reissue or extension thereon.

The claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

We claim:

1. A computer system, comprising:
    a first client computer having a first client computer processor unit in communication with a first client computer non-transitory memory element, wherein said first client computer includes a first tablet computer;
    a second client computer having a second client computer processor unit in communication with a second client computer non-transitory memory element, wherein said second client computer includes a second tablet computer, said first client computer having a first display surface and said second client computer having a second display surface;
    a server computer having a server processor in communication with a non-transitory server memory element configured to serve a plurality of electronic medical records associated with a patient identifier; and
    a dual graphical user interface program when executed by said first client computer or said second client computer functions to:
    depict a first graphical user interface on said first display surface of said first client computer, said first graphical user interface including a plurality of first graphical user interface images containing a plurality of data fields populatable with said plurality of electronic medical records associated with said patient identifier, each of said plurality of first graphical user interface images selectable by user interaction with one of a plurality of first interface index tabs in said first graphical user interface on said first display surface of said first client computer, wherein said plurality of first interface index tabs includes an encounters tab and a medical history tab;
    concurrently depict a second graphical user interface on said second display surface of said second client computer, said second graphical user interface including a plurality of second graphical user interface images containing a plurality of data input fields directly fillable by user interaction with data input elements related to said plurality of electronic medical records associated with said patient identifier, each of said plurality of second graphical user interface images selectable by user interaction with one of a plurality of second interface index tabs in said second graphical user interface on said second display surface of said second computer, wherein said plurality of second interface index tabs includes a progress note tab and an orders tab,
    wherein said dual graphical user interface program segregates user interaction with an electronic medical record associated with said patient identifier into two distinct parts, wherein viewing of said electronic medical record corresponds to said first graphical user interface and entry to the electronic medical record corresponds to said second graphical user interface;
    automatically couple one of said plurality of first graphical user interface images included in said first graphical user interface depicted on said first display surface of said first client computer with one of said plurality of second graphical user interface images included in said second graphical user interface depicted on said second display surface of said second client computer, wherein selection by user interaction with one of the corresponding plurality of second interface index tabs of said plurality of second graphical user interface images in said second graphical user interface depicted on said second display surface of said second client computer automatically causes depiction of said coupled one of said plurality of first graphical user interface images included in said first graphical user interface on said first display surface of said first client computer, wherein selection by user interaction with an uncoupled one of said plurality of first graphical user interface images causes depicting of said uncoupled one of said plurality of first graphical user interface images without affecting said one of said plurality of second graphical user interface images;
    correspondingly link a plurality of data input fields in said coupled one of said plurality of second graphical user interface images to a plurality of data fields depicted in said coupled one of said plurality of first graphical user interface images;
    automatically populate said plurality of data fields contained in said coupled one of said plurality of first graphical user interface images of said first graphical user interface with said plurality of electronic medical records associated with said patient identifier; and
    update said plurality of electronic medical records associated with said patient identifier populated in said plurality of data fields contained in said coupled one of said plurality of first graphical user interface images of said first graphical user interface by entry of said data input elements directly into said plurality of data input fields in said coupled one of said plurality of second graphical user interface images of said second graphical user interface.

2. The computer system of claim 1, wherein said dual graphical user interface program when executed by said first computer or said second computer further functions to translate said plurality of electronic medical records associated with said patient identifiers into a common format which can be segregated among said plurality of data fields of said plurality of first graphical user interface images included in said first graphical user interface.

3. The computer system of claim 2, wherein said dual graphical user interface program when executed by said first computer or said second computer further functions to concurrently update said plurality of data fields populated with said plurality of electronic medical records associated with said patient identifier depicted in said first graphical user interface with said data input elements entered directly into said plurality of data input fields included in said plurality of second graphical user interface images of said second graphical user interface.

4. The computer system of claim 3, wherein said dual graphical user interface program when executed by said first computer or said second computer further functions to depict uncoupled ones of said plurality of second graphical user interface images included in said second graphical user interface to overlay said one of said plurality of second graphical user interface images included in said second graphical user interface on said second display surface while coupled to said one of said plurality of first graphical user interface images included in said first graphical user interface on said first display surface.

5. The computer system of claim 4, wherein said dual graphical user interface program when executed by said first computer or said second computer further functions to depict uncoupled ones of said plurality of first graphical user interface images included in said first graphical user interface to overlay said one of said plurality of first graphical user interface images included in said first graphical user interface on said first display surface while coupled to said one of said plurality of second graphical user interface images included in said second graphical user interface on said second display surface.

6. The computer system of claim 5, wherein said dual graphical user interface program when executed by said first computer or said second computer further functions to uncouple said one of said plurality of second graphical user interface images included in said second graphical user interface coupled with said one of said plurality of first graphical user interface images included in said first graphical user interface, whereby subsequent depiction of said one said plurality of second graphical user interface images of said second graphical user interface on said second display surface does not cause depiction of a coupled one of said plurality of first graphical user interface images included in said first graphical user interface on said first display surface.

7. The computer system of claim 6, wherein said first client computer and said second client computer each further comprise a transceiver, and wherein said dual graphical user interface program when executed by said first computer or said second computer further functions to operate each said transceiver to exchange communication signals directly between said first and second client computers to operably coordinate functions of said first graphical user interface displayed on said first display surface with functions of said second graphical user interface displayed on said second display surface.

8. The computer system of claim 7, wherein said dual graphical user interface program when executed by said first computer or said second computer further functions to:
configure said second client computer as a client computer image capture device capable of capturing an image;
configure said first client computer to receive said image captured by said second client computer configured as said client computer image capture device;
associate said image captured by said second client computer configured as said client computer image capture device with said plurality of electronic medical records associated with said patient identifier;
wirelessly connect said first client computer to said second client computer; and
depict said image captured by said second client computer configured as said client computer image capture device in said first graphical user interface.

9. The computer system of claim 7, wherein said dual graphical user interface program when executed by said first computer or said second computer further functions to:
depict a plurality of patient identifiers in one of said plurality of second graphical user interface images included in said second graphical user interface, each one of said plurality of patient identifiers selectable by user interaction to cause retrieval of said plurality of electronic medical records associated with a selected one of said plurality of patient identifiers;
retrieve said plurality of electronic medical records associated with said selected one of said plurality of patient identifiers;
depict an encounters interface image as one of said plurality of first graphical user interface images depicted in said first graphical user interface;
concurrently depict a progress note interface image associated with a selected one of said plurality of patient identifiers as one of said plurality of second graphical user interface images depicted in said second graphical user interface.

10. The computer system of claim 9, wherein said progress note interface image includes:
said plurality of data input fields each directly fillable by user interaction with said data input elements; and
a submit control icon which by user interaction stores said data input elements to said plurality of electronic medical records associated with said selected one of said plurality of patient identifiers, wherein said dual graphical user interface program concurrently depicts said data input elements in said plurality of data fields of said plurality of first graphical user interface images populated with said plurality of electronic medical records associated with said patient identifier.

11. The computer system of claim 10, wherein said plurality of first graphical user interface images includes a patient education interface image including a patient education document list having a plurality of patient education document selection elements selectable by user interaction to depict a patient education document in said second graphical user interface.

12. The computer system of claim 11, wherein said first client computer having said first display surface is operated a distance from said second client computer having said second display surface, said first graphical user interface depicted on said first display surface interactive with a first user, said second graphical user interface interactive with a second user.

13. The computer system of claim 12, wherein said dual graphical user interface program when executed by said first computer or said second computer further functions to depict a patient education document movement control icon which by user interaction allows said patient education document to reciprocally pass between said first graphical user interface and said second graphical user interface.

14. The computer system of claim 13, wherein said dual graphical user interface program when executed by said first computer or said second computer further functions to:
pass a first patient education document from said first graphical user interface to said second graphical user interface;
retrieve a second patient education document selected by said second user; and
depict said second patient education document in said first graphical user interface.

15. The computer system of claim 14, wherein said second graphical user interface image comprises a prescriptions graphical user interface image having said data input fields fillable by user interaction with a prescription for a medication.

16. The computer system of claim 15, wherein said dual graphical user interface program when executed by said first computer or said second computer further functions to:
compare said prescription entered into said data input fields to prescription equivalents contained in a prescription database;
depict said prescription associated with a prescription price in said second graphical user interface;
depict said prescription equivalents associated with prescription equivalents prices in said second graphical user interface.

17. The computer system of claim 16, wherein said dual graphical user interface program when executed by said first computer or said second computer further functions to depict sensorially perceivable prescription price comparison indicia in said second graphical user interface, said sensorially perceivable prescription price comparison indicia varying based on comparison of said prescription price against said prescription equivalents prices, wherein variance of said sensorially perceivable prescription price comparison indicia distinguish at least between said prescription price being greater than said prescription equivalents prices or being lesser than said prescription equivalents prices.

18. The computer system of claim 17, wherein said dual graphical user interface program when executed by said first computer or said second computer further functions to:
compare said prescription or said prescription equivalents entered into said data input field against an insured prescriptions database containing insured prescriptions;
depict said insured prescriptions in said second graphical user interface;
depict insured prescription equivalents in said second graphical user interface.

19. The computer system of claim 18, wherein said dual graphical user interface program when executed by said first computer or said second computer further functions to depict said sensorially perceivable prescription price comparison indicia in said second graphical user interface, said sensorially perceivable prescription price comparison indicia varying based on comparison of said prescription or said prescription equivalents against said insured prescriptions database containing insured prescriptions or insured prescription equivalents, wherein variance of said sensorially perceivable prescription price comparison indicia distinguishes at least between said prescription or said prescription equivalents being insured or not insured by an insurer associated with said selected one of said plurality of patient identifiers.

20. The computer system of claim 18, wherein variance of said sensorially perceivable prescription price comparison indicia distinguish at least between said prescription price being greater than insured prescription equivalents prices or being lesser than said insured prescription equivalents prices.

* * * * *